United States Patent [19]
Hiramatsu et al.

[11] Patent Number: 5,919,647
[45] Date of Patent: Jul. 6, 1999

[54] METHODS AND APPARATUSES FOR EXAMINING PATHOGEN RESISTANCE OF PLANT, FOR EVALUATING ABILITY TO IMPART PATHOGEN RESISTANCE TO PLANT, AND FOR EVALUATING AGRICULTURAL CHEMICAL

[75] Inventors: Mitsuo Hiramatsu; Kazuyoshi Ohta, both of Hamamatsu; Takahiro Makino; Kimihiko Kato, both of Iwata-gun; Sakio Suzuki, deceased, late of Hamamatsu, all of Japan, by Kae Suzuki. Masumi Nakamichi, Takayuki Suzuki, legal representatives

[73] Assignees: Hamamatsu Photonics K.K., Hamamatsu; Shizuoka Prefecture, Shizuoka, both of Japan

[21] Appl. No.: 08/924,119

[22] Filed: Sep. 5, 1997

Related U.S. Application Data

[63] Continuation of application No. 08/474,088, Jun. 7, 1995, abandoned, which is a continuation-in-part of application No. 08/136,202, Oct. 15, 1993, abandoned.

[30] Foreign Application Priority Data

Oct. 16, 1992 [JP] Japan .................................. 4-279042

[51] Int. Cl.$^6$ .............................. C12Q 1/02; C12M 1/34
[52] U.S. Cl. ..................... 435/29; 435/287.1; 435/288.7; 435/8; 435/30; 436/63
[58] Field of Search .............................. 435/4, 8, 29, 30, 435/31, 32, 33, 34, 35, 39, 40, 287.7, 288.7; 436/808, 809, 63; 422/82.05, 82.07, 52; 356/319, 435, 229, 232, 433, 432; 250/578.1, 239, 459.1, 461.2, 462.1; 47/58

[56] References Cited

U.S. PATENT DOCUMENTS

| | | |
|---|---|---|
| 430,150 | 6/1890 | Popp ................................... 435/288.7 |
| 3,520,660 | 7/1970 | Webb . |
| 4,396,579 | 8/1983 | Schroeder et al. . |
| 4,458,531 | 7/1984 | Mehlhardt et al. ...................... 436/63 |

FOREIGN PATENT DOCUMENTS

| | | |
|---|---|---|
| 0 492 961 | 7/1992 | European Pat. Off. . |
| 2686350 | 7/1993 | France . |
| 367143 | 2/1771 | U.S.S.R. . |
| 1160998 | 6/1985 | U.S.S.R. . |
| 1166729 | 7/1985 | U.S.S.R. . |
| 1217302 | 3/1986 | U.S.S.R. . |
| 1630705 | 2/1991 | U.S.S.R. . |
| 1683581 | 10/1991 | U.S.S.R. . |
| 2 212 915 | 8/1989 | United Kingdom . |
| 91/17266 | 11/1991 | WIPO . |

OTHER PUBLICATIONS

English language translation of EP 430 150 (Sep. 1996).
Database WPI, Section Ch, Week 9349, Derwent Publications Ltd., London, GB; Class A01, AN93–393829 & SU–A–1 777 726 (Agric. Biotech. Res. Des. Tech. Inst.), Nov. 30, 1992.

*Primary Examiner*—William H. Beisner
*Attorney, Agent, or Firm*—Cushman Darby & Cushman Intellectual Property Group of Pillsbury Madison & Sutro, LLP

[57] ABSTRACT

An apparatus including: a sprayer for inoculating a microbe on a first division divided from at least one sample of a plant to be examined; sample leaving device for leaving a second division divided from the sample not inoculated with the microbe and the first division inoculated with the microbe, for a predetermined period of time under a predetermined condition; first and second photodetector for respectively measuring the quantities of luminescence emitted from the first and second divisions which have been left standing by the sample leaving device; and a computer for comparing the quantities of the luminescence measured by the first and second photodetector, thereby to examine the resistance or susceptibility of the plant to the microbe.

7 Claims, 8 Drawing Sheets

DYNAMICS OF BIOLUMINESCENCE IN OXIDATIVE PAROCESS DURING ELICITATION OF RADISH STORAGE ROOT POURED WITH 0.4mL OF 0.1mM DIGITONIN ENHANCEMENT BY 0.1mM DBPH, 10mM SALICYLIC ACID ENHANCEMENT BY 0.1mM DBPH, 0.1mM DIGITONIN, 10mM SALICYLIC ACID, 0.1mM DBPH AND CONTROL.

METHODS AND APPARATUSES FOR EXAMINING PATHOGEN RESISTANCE OF PLANT, FOR EVALUATING ABILITY TO IMPART PATHOGEN RESISTANCE TO PLANT, AND FOR EVALUATING AGRICULTURAL CHEMICAL

RELATED APPLICATION

This is a continuation of application Ser. No. 08/474,088, filed on Jun. 7, 1995, which was abandoned upon the filing hereof which is a CIP of application Ser. No. 08/136,202, filed on Oct. 15, 1993, now abandoned.

BACKGROUND OF THE INVENTION

1. Field of the Invention

The present invention relates to a method and an apparatus for examining resistance of a plant to pathogen (or pathogenic microbe), a method and an apparatus for evaluating ability of a microbe (such as nonpathogenic strain or weak pathogenic strain) to impart pathogen resistance to a plant, and a method and an apparatus for evaluating ability of an agricultural chemical to activate pathogen resistance of a plant.

2. Related Background Art

The natural environment of Japan is suitable for growth of agricultural products, and on the other hand, also suitable for growth of pathogens or pathogenic microbe for various plants, such as molds (or mold fungi), bacteria and viruses. The prevention of disease due to such pathogens by pathogen-resistant varieties is very significant in view of a measure for reducing production cost of agricultural products, as well as health care (or health management) for humans.

As a method for examining the pathogen resistance or pathogen susceptibility (or sensitivity) of a plant, the following method has heretofore been used.

First, various pathogens are inoculated into seedlings or young plants to be examined.

Next, various symptoms caused in the seedlings by the above-mentioned inoculation, such as putrefaction (or rotting), spots, blight and wilting, are observed to examine the pathogen resistance and pathogen susceptibility of the plant.

This method is also used for screening a nonpathogenic strain or weak pathogenic strain capable of imparting resistance to a plant, or an agricultural chemical capable of imparting resistance to a plant.

However, this method has the following problems.

First, this method takes a very long time to provide examination results. In a case where a plant is bred without vegetative reproduction, the plant is generally grown from a seed. In this case, it will take about 3 weeks to grow a seedling from the seed, while it depends on the kind of plant. In addition, it takes about 1 to 4 weeks for a symptom to appear after various pathogens, agricultural chemicals, etc., are inoculated into the seedling. Accordingly, it takes at least about 1 to 2 months in total to obtain results in a case where the seedling is grown from the seed.

Second, the above method requires much labor and a vast site. A symptom appearing in the seedling varies depending on a combination of a plant, a pathogen and an agricultural chemical, and there is a large difference in the symptom between individual samples of the plant. Accordingly, for the purpose of statistic processing, it is necessary to cultivate a large number of samples of the plant. Thus, in order to cultivate such a large number of samples of the plant, much labor and a vast site are required.

Third, when the above method is used, the resultant symptoms appearing in individual seedlings cannot be measured quantitatively. In general, such symptoms are visually observed with eyes, and such visual observation largely depends on the experiences of observers, and much skill is required in order to obtain objective results.

Fourth, when the symptom is simply observed, it is difficult to recognize the internal state or condition in the inside of a plant. In order to recognize the internal state or condition of the plant, it is necessary to use a biochemical analysis technique, such as liquid chromatography and centrifugal method, for the purpose of measuring or analyzing various enzyme activities, specific protein peculiar to infection, etc. Such measurement requires much labor and a heavy monetary burden, and further requires a high-level technique.

Fifth, when the above method is used, it is very difficult to control the environment or ambient conditions under which the plant is to be examined. The resistance of a plant to a pathogen is highly susceptible to ambient conditions such as temperature, length of daytime, ultraviolet rays and visible rays. Accordingly, when samples of a plant are examined, it is necessary to place the samples to be examined under the same ambient conditions, However, when the above-mentioned conventional method is used, it is difficult to place the plants to be examined under the same ambient conditions.

Accordingly, an object of the present invention is to provide a method and/or apparatus for examining pathogen resistance (or pathogen susceptibility) of a plant, which have solved the above-mentioned problems.

Another object of the present invention is to provide a method and/or apparatus for evaluating an ability of a microbe (such as non-pathogenic strain and weak-pathogenic strain) to impart pathogen resistance to a plant, which have solved the above-mentioned problems.

A further object of the present invention is to provide a method and/or apparatus for evaluating an agricultural chemical which is capable of activating pathogen resistance of a plant, which have solved the above-mentioned problems.

As a result of the present inventors' study, it has been found that when a pathogen intrudes into a plant, and the plant reacts to the pathogen which has intruded thereinto, a change in ultra-weak luminescence is observed in accordance with the kind of the pathogen and the amount of the inoculation thereof. Based on such a discovery, the present inventors have developed a method and an apparatus which have solved the above-mentioned problems encountered in the prior art.

More specifically, according to a first aspect of the present invention, there is provided a method and an apparatus for optically examining pathogen resistance of a plant. According to a second aspect of the present invention, there is provided a method and an apparatus for optically evaluating an ability of a microbe such as nonpathogenic strain and weak-pathogenic strain to impart pathogen resistance to a plant. According to a third aspect of the present invention, there is provided a method and an apparatus for optically evaluating an agricultural chemical which is capable of activating pathogen resistance of a plant.

Japanese Laid-Open Patent Application No. 72802/1990 (Hei 2-72802) discloses a method for determining a condition of a plant by using ultra-weak luminescence. However, this method is one for determining degree of deterioration and germination potential of a plant seed. Accordingly, this method cannot solve the above-described problems.

SUMMARY OF THE INVENTION

According to the present invention, there is provided a method for examining pathogen resistance or pathogen susceptibility of a plant, comprising the steps of:

dividing at least one sample of a plant to be examined into at least two divisions, inoculating a pathogen on a first division of the at least two divisions of the sample, leaving the first division standing for a predetermined period of time under a predetermined condition, and measuring the quantity of luminescence emitted from the first division;

leaving a second division of the at least two divisions of the sample for a predetermined period of time under a predetermined condition while inoculating substantially no pathogen on the second division of the sample, and measuring the quantity of luminescence emitted from the second division; and comparing the quantities of the luminescence emitted from the first and second divisions of the sample, thereby to examine the resistance or susceptibility of the plant to the pathogen.

The present invention also provides an apparatus for examining pathogen resistance or pathogen susceptibility of a plant, comprising:

first sample positioning means for positioning a first division divided from at least one sample of a plant to be examined;

second sample positioning means for positioning a second division divided from the sample of the plant;

inoculating means for inoculating a pathogen on the first division;

sample leaving means for leaving the second division positioned by the second sample positioning means and the first division inoculated with the pathogen and positioned by the first sample positioning means, for a predetermined period of time under a predetermined condition;

first photodetecting means disposed opposite to the first sample positioning means for measuring the quantity of luminescence emitted from the first division which has been left standing by the sample leaving means;

second photodetecting means disposed opposite to the second sample positioning means for measuring the quantity of luminescence emitted from the second division which has been left standing by the sample leaving means; and examining means for comparing the quantities of the luminescence measured by the first and second photodetecting means, thereby to examine the resistance or susceptibility of the plant to the pathogen.

The present invention further provides an apparatus for examining pathogen resistance or pathogen susceptibility of a plant, comprising:

first sample positioning means for positioning a first division divided from at least one sample of a plant to be examined;

second sample positioning means for positioning a second division divided from the sample of the plant;

inoculating means for inoculating a pathogen on the first division;

sample leaving means for leaving the second division positioned by the second sample positioning means and the first division inoculated with the pathogen and positioned by the first sample positioning means, for a predetermined period of time under a predetermined condition;

a photodetector disposed so as to be opposed alternately to either of the first and the second sample positioning means for detecting luminescence emitted from either of the first and second divisions which have been left standing by the sample leaving means;

measuring means for alternately receiving an output from the photodetector in synchronism with switching of the first and second sample positioning means to be disposed opposite to the photodetector, thereby to respectively measure the quantities of luminescence emitted from the first and second divisions; and examining means for comparing the quantities of the luminescence respectively emitted from the first and second divisions, which have been measured by the measuring means, thereby to examine the resistance or susceptibility of the plant to the pathogen.

The present invention further provides a method for evaluating an ability of a microbe (such as non-pathogenic strain and weak-pathogenic strain) to impart pathogen resistance to a plant, comprising the steps of:

dividing at least one sample of a plant into at least two division, inoculating a microbe to be examined on a first division of the at least two divisions of the sample, leaving the first division standing for a predetermined period of time under a predetermined condition, and measuring the quantity of luminescence emitted from the first division;

leaving a second division of the at least two divisions of the sample for a predetermined period of time under a predetermined condition while inoculating substantially no microbe to be examined on the second division, and measuring the quantity of luminescence emitted from the second division of the plant; and comparing the quantities of the luminescence emitted from the first and second divisions of the sample, thereby to examine the ability of the microbe to impart pathogen resistance to the plant.

The present invention further provides an apparatus for examining an ability of a microbe (such as non-pathogenic strain and weak-pathogenic strain) to impart pathogen resistance to a plant, comprising:

first sample positioning means for positioning a first division divided from at least one sample of a plant;

second sample positioning means for positioning a second division divided from the sample of the plant;

inoculating means for inoculating a microbe to be examined on the first division;

sample leaving means for leaving the second division positioned by the second sample positioning means and the first division inoculated with the microbe and positioned by the first sample positioning means, for a predetermined period of time under a predetermined condition;

first photodetecting means disposed opposite to the first sample positioning means for measuring the quantity of luminescence emitted from the first division which has been left standing by the sample leaving means;

second photodetecting means disposed opposite to the second sample positioning means for measuring the quantity of luminescence emitted from the second division which has been left standing by the sample leaving means; and examining means for comparing the quantities of the luminescence respectively emitted from the first and second divisions, which have been measured by the first and second photodetecting means, thereby to examine the ability of the microbe to impart pathogen resistance to the plant.

The present invention further provides an apparatus for examining an ability of a microbe (such as non-pathogenic strain and weak-pathogenic strain) to impart pathogen resistance to a plant, comprising:

first sample positioning means for positioning a first division divided from at least one sample of a plant;

second sample positioning means for positioning a second division divided from the sample of the plant;

inoculating means for inoculating a microbe to be examined on the first division;

sample leaving means for leaving the second division positioned by the second sample positioning means and the first division inoculated with the microbe and positioned by the first sample positioning means, for a predetermined period of time under a predetermined condition;

a photodetector disposed so as to be opposed alternately to either of the first and the second sample positioning means for detecting luminescence emitted from either of the first and second divisions which have been left standing by the sample leaving means;

measuring means for alternately receiving an output from the photodetector in synchronism with switching of the first and second sample positioning means to be disposed opposite to the photodetector, thereby to measure the quantities of luminescence respectively emitted from the first and second divisions; and examining means for comparing the quantities of the luminescence respectively emitted from the first and second divisions, which have been measured by the measuring means, thereby to examine the ability of the microbe to impart pathogen resistance to the plant.

The present invention further provides a method for evaluating ability of an agricultural chemical to activate pathogen resistance of a plant, comprising the steps of:

dividing at least one sample of a plant into at least two divisions, causing a first division of the at least two divisions of the sample to absorb an agricultural chemical, leaving the first division standing for a predetermined period of time under a predetermined condition, inoculating a pathogen on the first division, leaving the first division standing for a predetermined period of time under a predetermined condition, and measuring the quantity of luminescence emitted from the first division;

leaving a second division of the at least two divisions of the sample for a predetermined period of time under a predetermined condition while causing the second division to absorb substantially no agricultural chemical, inoculating the pathogen on the second division, leaving the second division standing for a predetermined period of time under a predetermined condition, and measuring the quantity of luminescence emitted from the second division; and comparing the quantities of the luminescence respectively emitted from the first and second divisions of the sample, thereby to examine the ability of the agricultural chemical to activate pathogen resistance of the plant.

The present invention further provides an apparatus for evaluating ability of an agricultural chemical to activate pathogen resistance of a plant, comprising:

first sample positioning means for positioning a first division divided from at least one sample of a plant;

second sample positioning means for positioning a second division divided from the sample of the plant;

absorbing means for causing the first division to absorb an agricultural chemical;

first sample leaving means for leaving the second division positioned by the second sample positioning means, and the first division positioned by the first sample positioning means having absorbed the agricultural chemical, for a predetermined period of time under a predetermined condition;

inoculating means for inoculating a pathogen on the second division having been left standing by the first sample leaving means, and the first division having absorbed the agricultural chemical and having been left standing by the first sample leaving means;

second sample leaving means for leaving the second division positioned by the second sample positioning means and inoculated with the pathogen, and the first division positioned by the first sample positioning means which has absorbed the agricultural chemical and has been inoculated with the pathogen, for a predetermined period of time under a predetermined condition;

first photodetecting means disposed opposite to the first sample positioning means for measuring the quantity of luminescence emitted from the first division which has been left standing by the second sample leaving means;

second photodetecting means disposed opposite to the second sample positioning means for measuring the quantity of luminescence emitted from the second division which has been left standing by the second sample leaving means; and examining means for comparing the quantities of the luminescence respectively emitted from the first and second divisions, which have been measured by the first and second photodetecting means, thereby to examine the ability of the agricultural chemical to activate pathogen resistance of the plant.

The present invention further provides an apparatus for examining ability of an agricultural chemical to activate pathogen resistance of a plant, comprising:

first sample positioning means for positioning a first division divided from at least one sample of a plant;

second sample positioning means for positioning a second division divided from the sample of the plant;

absorbing means for causing the first division to absorb an agricultural chemical;

first sample leaving means for leaving the second division positioned by the second sample positioning means, and the first division positioned by the first sample positioning means and having absorbed the agricultural chemical, for a predetermined period of time under a predetermined condition;

inoculating means for inoculating a pathogen on the second division having been left standing by the first sample leaving means, and the first division having absorbed the agricultural chemical and having been left standing by the first sample leaving means;

second sample leaving means for leaving the second division positioned by the second sample positioning means and inoculated with the pathogen, and the first division positioned by the first sample positioning means which has absorbed the agricultural chemical and has been inoculated with the pathogen, for a predetermined period of time under a predetermined condition;

a photodetector disposed so as to be opposed alternately to either of the first and the second sample positioning means, for detecting luminescence emitted from either of the first and second divisions which have been left standing by the second sample leaving means;

measuring means for alternately receiving an output from the photodetector in synchronism with switching of the first and second sample positioning means to be disposed opposite to the photodetector, thereby to measure the quantities of luminescence respectively emitted from the first and second divisions; and examining means for comparing the quantities of the luminescence respectively emitted from the first and second divisions, which have been measured by the measuring means, thereby to examine the ability of the agricultural chemical to activate pathogen resistance of the plant.

According to the above-mentioned method for examining pathogen resistance or pathogen susceptibility of a plant, at least one sample of a plant to be examined is divided or classified into at least two divisions. One division (first division) of the at least two divisions is inoculated with a pathogen while another division (second division) of the at least two divisions is not substantially inoculated with the pathogen, and the first and second divisions are left standing for a predetermined period of time under a predetermined condition. Accordingly, a difference is provided between the first and second divisions in the quantity (or amount) of luminescence (e.g., ultra-weak luminescence) emitted from the first and second divisions, depending on the degree of an interaction between the plant and the pathogen. In this method according to the present invention, the quantities of the luminescence emitted from these divisions of the plant to be examined are measured, and the thus measured quantities of the luminescence are compared with each other, whereby pathogen resistance or pathogen susceptibility of the plant to be examined can easily be examined for a short period of time, and the examination can be conducted objectively.

The above-mentioned first apparatus for examining pathogen resistance or pathogen susceptibility of a plant comprises inoculating means for inoculating a pathogen on a first division divided from at least one sample of a plant to be examined; sample leaving means for leaving the first division inoculated with the pathogen and a second division (divided from the sample of the plant) not inoculated with the pathogen, for a predetermined period of time under a predetermined condition; first and second photodetecting means for respectively measuring the quantities of luminescence (e.g, ultra-weak luminescence) emitted from the first and second divisions which have been left standing by the sample leaving means; and examining means for comparing the quantities of the luminescence respectively measured by the first and second photodetecting means, thereby to examine the resistance or susceptibility of the plant to the pathogen. Accordingly, when such an apparatus is used, the first division inoculated with the pathogen and the second division not inoculated with the pathogen may be treated under the same environment (or ambient conditions), and the luminescence emitted from these divisions may be measured simultaneously and easily for a short period of time. As a result, pathogen resistance or pathogen susceptibility of the plant can be examined objectively and accurately.

The above-mentioned second apparatus for examining pathogen resistance or pathogen susceptibility of a plant comprises: first and second sample positioning means for respectively positioning a first division and a second division divided from at least one sample of a plant to be examined; inoculating means for inoculating a pathogen on the first division; and sample leaving means for leaving the second division positioned by the second sample positioning means and the first division inoculated with the pathogen and positioned by the first sample positioning means, for a predetermined period of time under a predetermined condition. Accordingly, when such an apparatus is used, the first division inoculated with the pathogen and the second division not inoculated with the pathogen may be treated under the same environment (or ambient conditions). This apparatus further comprises a photodetector disposed so as to be opposed alternately to either one of the first and the second sample positioning means for detecting luminescence emitted from either of the first and second divisions which have been left standing by the sample leaving means; measuring means for alternately receiving an output of the photodetector in synchronism with switching of the first and second sample positioning means to be disposed opposite to the photodetector, thereby to respectively measure the quantities of luminescence emitted from the first and second divisions; and examining means for comparing the quantities of the luminescence measured by the measuring means, thereby to examine the resistance or susceptibility of the plant to the pathogen. Accordingly, when this apparatus is used, the luminescence emitted from the first and second divisions may be measured substantially simultaneously for a short period of time, even by use of a single photodetector.

According to the above-mentioned method for evaluating an ability of a microbe (such as non-pathogenic strain and weak pathogenic strain) to impart pathogen resistance to a plant, at least one sample of a plant is divided or classified into at least two divisions, one of the at least two divisions (first division) is inoculated with a microbe to be examined while the another division (second division) is not inoculated with the microbe, and the first and second divisions are left standing for a predetermined period of time under a predetermined condition. In this method, the quantities of luminescence (e.g., ultra-weak luminescence) emitted from the divisions may be measured depending on the degree of the pathogen resistance of the plant imparted by the inoculation of the microbe, and the thus measured quantities of the luminescence are compared with each other. Accordingly, the ability of the microbe to impart pathogen resistance to the plant may be evaluated easily for a short period of time, and such evaluation can be conducted objectively and accurately.

The above-mentioned first apparatus for examining an ability of a microbe (such as non-pathogenic strain and weak pathogenic strain) to impart pathogen resistance to a plant, comprises: inoculating means for inoculating a microbe to be examined on a first division divided from at least one sample of a plant; sample leaving means for leaving the first division inoculated with the microbe and the second division not inoculated with the microbe, for a predetermined period of time under a predetermined condition; first and second photodetecting means for respectively measuring the quantities of luminescence emitted from the first and second divisions which have been left standing by the sample leaving means; and examining means for comparing the quantities of the luminescence respectively measured by the first and second photodetecting means, thereby to examine the ability of the microbe to impart pathogen resistance to the plant.

Accordingly, when such an apparatus is used, the first division inoculated with the microbe and the second division not inoculated with the microbe may be treated under the same environment, and the luminescence emitted from the first and second divisions can be measured simultaneously and easily for a short period of time. Accordingly, ability of the microbe to impart pathogen resistance to the plant can be evaluated objectively and accurately.

The above-mentioned second apparatus for examining an ability of a microbe (such as non-pathogenic strain and weak pathogenic strain) to impart pathogen resistance to a plant, comprises: first and second sample positioning means for respectively positioning a first division and a second division divided from at least one sample of a plant; inoculating means for inoculating a microbe to be examined on the first division; and sample leaving means for leaving the first division inoculated with the microbe and the second division not inoculated with the microbe, for a predetermined period of time under a predetermined condition.

Accordingly, when such an apparatus is used, the first division inoculated with the pathogen and the second division not inoculated with the pathogen may be treated under the same environment.

This apparatus further comprises: a photodetector disposed so as to be opposed alternately to either of the first and second sample positioning means for detecting luminescence emitted from either of the first and second divisions which have been left standing by the sample leaving means; measuring means for alternately receiving an output of the photodetector in synchronism with switching of the first and second sample positioning means to be disposed opposite to the photodetector, thereby to measure the quantities of luminescence respectively emitted from the first and second divisions; and examining means for comparing the quantities of the luminescence measured by the measuring means, thereby to examine the ability of the microbe to impart pathogen resistance to the plant.

Accordingly, when this apparatus is used, the luminescence emitted the first and second divisions may be measured substantially simultaneously for a short period of time, even by use of a single photodetector.

In the above-mentioned method for evaluating ability of an agricultural chemical to activate pathogen resistance of a plant, at least one sample a plant is divided or classified into at least two divisions, and one division(first division) of the at least two divisions is caused to absorb an agricultural chemical while another division(second division) is not caused to absorb the agricultural chemical, and the first and second divisions are left standing for a predetermined period of time under a predetermined condition. Then, the first and second divisions are inoculated with a pathogen, and are left standing for a predetermined period of time under a predetermined condition. Accordingly, a difference is provided between the first and second divisions in the quantity of luminescence emitted from these divisions depending on the degree of activation of pathogen resistance of the plant based on the absorption of the agricultural chemical.

In this method, the quantities of the luminescence emitted from the first and second divisions are measured, and the thus measured quantities of the luminescence are compared with each other. Accordingly, the ability of the agricultural chemical to activate pathogen resistance of the plant can easily be evaluated for a short period of time, and such evaluation can be conducted objectively.

The above-mentioned first apparatus for evaluating ability of an agricultural chemical to activate pathogen resistance of a plant, comprises: absorbing means for causing a first division divided from at least one sample of a plant to absorb an agricultural chemical; first sample leaving means for leaving the first division having absorbed the agricultural chemical and the second division not having absorbed the agricultural chemical, for a predetermined period of time under a predetermined condition; inoculating means for inoculating a pathogen on the first and second divisions; second sample leaving means for leaving the second division inoculated with the pathogen and the first division having absorbed the agricultural chemical and having been inoculated with the pathogen, for a predetermined period of time under a predetermined condition; first and second photodetecting means for respectively measuring the quantities of luminescence emitted from the first and second divisions having been left standing by the second sample leaving means; and examining means for comparing the quantities of the luminescence measured by the first and second photodetecting means, thereby to examine the ability of the agricultural chemical to activate pathogen resistance of the plant.

Accordingly, when such an apparatus is used, the first division having absorbed the agricultural chemical and the second division not having absorbed the agricultural chemical may be treated under the same environment, and the luminescence emitted from these divisions can be measured simultaneously and easily for a short period of time. As a result, such evaluation can be conducted objectively and accurately.

The above-mentioned second apparatus for examining ability of an agricultural chemical to activate pathogen resistance of a plant, comprises: first and second sample positioning means for respectively positioning a first division and a second division divided from at least one sample of a plant; absorbing means for causing the first division to absorb an agricultural chemical; first sample leaving means for leaving the first division having absorbed the agricultural chemical and the second division not having absorbed the agricultural chemical, for a predetermined period of time under a predetermined condition; inoculating means for inoculating a pathogen on the first and second divisions; and second sample leaving means for leaving the second division inoculated with the pathogen and the first division having absorbed the agricultural chemical and having been inoculated with the pathogen, for a predetermined period of time under a predetermined condition.

Accordingly, when such an apparatus is used, the first division having absorbed the agricultural chemical and the second division not having absorbed the agricultural chemical may be treated under the same environment.

This apparatus further comprises: a photodetector disposed so as to be opposed alternately to either of the first and the second sample positioning means, for detecting luminescence emitted from either of the first and second divisions which have been left standing by the second sample leaving means; measuring means for alternately receiving an output of the photodetector in synchronism with switching of the first and second sample positioning means to be disposed opposite to the photodetector, thereby to measure the quantities of luminescence respectively emitted from the first and second divisions; and examining means for comparing the quantities of the luminescence measured by the measuring means, thereby to examine the ability of the agricultural chemical to activate pathogen resistance of the plant.

Accordingly, when this apparatus is used, the luminescence emitted the first and second divisions may be measured substantially simultaneously for a short period of time, even by use of a single photodetector.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art form this detailed description.

DESCRIPTION OF PREFERRED EMBODIMENTS

Figure 1:
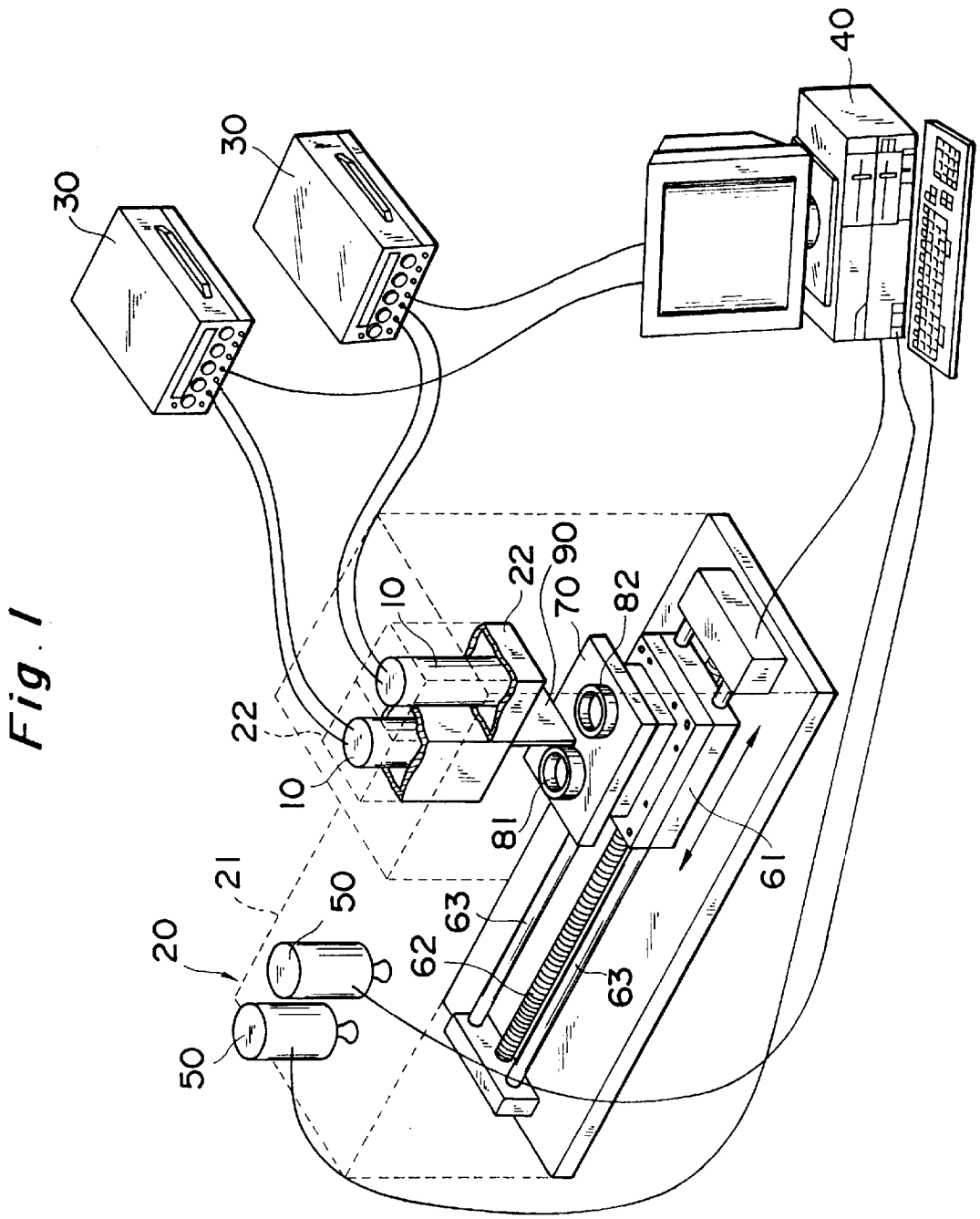
FIG. 1 is a schematic perspective view showing the structure of an apparatus according to a first embodiment of the present invention.

Before the description of preferred embodiments of the present invention, the principle of the present invention will be explained.

It is known that when a plant is in a state of sprouting, ultra-weak luminescence (radiation of light) emitted therefrom is observed. As a result of earnest study, the present inventors have found that when a pathogen is intruding into a plant, the plant show a positive protective reaction, with a result that luminescence is observed. Especially, when the interaction between the plant and the pathogen is strong to a certain extent, the quantity (or amount) of the resultant luminescence is increased with specificity (or peculiarly or selectively), as compared with an ordinary quantity of such luminescence. Between these quantities of luminescence, a significant or meaningful difference has been observed by the present inventors.

According to the present inventors' study, in a case where an individual plant is physically divided into at least two parts (first and second parts), or a plurality of samples of a plant of one kind are classified or divided into at least two groups (first and second groups), one of these parts or groups is inoculated with a pathogen while the other parts or group is not substantially inoculated with the pathogen, and the resultant luminescence is observed, a significant difference is provided between the quantities of luminescence emitted from the first and second parts (or groups) in some cases, while a significant difference is not provided in the other cases. According to the present inventors' investigation, it has been found that such a significant difference in the quantity of luminescence is provided when the plant has pathogen resistance of not lower than a certain level; and a significant difference is not provided when the plant has pathogen resistance at a low level.

According to the present inventors' study, pathogen resistance of a plant may be examined on the basis of the principle as described above. The present invention is based on such a discovery. According to the present inventor's study; it has also been found that an ability of a microbe (such as non-pathogenic strain and weak-pathogenic strain) to impart pathogen resistance to a plant may be evaluated on the basis of a principle similar to that as described above. According to the present inventor's study, it has further been found that an ability of an agricultural chemical to activate pathogen resistance of a plant may be evaluated on the basis of a principle similar to that as described above.

Hereinbelow, the present invention will be described in more detail.

The method for examining pathogen resistance of a plant according to the present invention which is capable of examining the resistance or susceptibility of a plant to be examined to a pathogen may preferably be conducted in the following manner.

First, a sample (or a plurality of samples) of a plant to be examined is divided into at least two divisions (i.e., at least two parts of a sample of a plant, or at least two groups of a plurality of samples of a plant). The plant to be examined usable in the present invention may be the entirety of a plant or a portion of a plant, as long as it is capable of emitting ultra-weak luminescence (so-called "biophoton"). It is known that various plants or their parts are capable of emitting biophoton (e.g., as described in Experientia, Vol. 44, pp. 550–559 (1988)). In the present invention, in view of easiness in the measurement of biophoton, it is preferred to use a plant or a portion thereof wherein cell division occurs. Specific examples of such a plant or a portion thereof relating to (or causing) cell division may include: germinating or growing plant or a portion thereof such as germinating plant seed and growing plant root.

Then, a pathogen is inoculated on or into one of the above-mentioned at least two divisions (first division). The first division of the sample is left standing for a predetermined period of time and under a predetermined condition which are sufficient for the pathogen to react with the first division of the sample, and thereafter the quantity of luminescence (e.g., ultra-weak luminescence) emitted from the first division (first pathogen-inoculated sample) of the plant to be examined is measured (first step). At this time, the above luminescence may preferably be measured after a somewhat long period of time counted from the inoculation of the microbe (such as the above-mentioned pathogen), since the luminescence to be measured in the present invention is luminescence based on a protective reaction of a plant to be examined against the inoculation of the microbe. In the present invention, it is preferred that the luminescence emitted from the plant to be examined is preliminarily measured with the elapse of time so as to estimate the state of a time-dependent change in the luminescence, and the interval or period of time between the inoculation of the microbe and the measurement of the luminescence may be changed, as desired, so as to measure the luminescence in the neighborhood of the maximum (or at the maximum) thereof. In the present invention, the above-mentioned period of time between the inoculation of the microbe and the measurement of the luminescence may preferably be about one (1) hour or longer, more preferably four (4) hours or longer (particularly preferably, 10 hours or longer).

Here, an average value of the quantities of luminescence from the first pathogen-inoculated sample is represented by $S_1$ (counts/sec), and a standard error (SEM) of the quantities is represented by $n_1$ (counts/sec). Herein, the above-mentioned standard error is a value determined by the following equation, i.e., a value obtained by dividing standard deviation (SD) by a square root of the number of samples (N) or the number of data (number of data acquisition operations) obtained by luminescence measurement.

Standard Error (SEM)=$SD/N^{1/2}$, wherein SD denotes a standard deviation, and N denotes the number of data obtained by luminescence measurement. In the present invention, in view of the reproducibility or accuracy of the resultant measurement data, the above-mentioned number of data (N) may preferably be 100 or more, more preferably 400 or more (particularly preferably, 900 or more). With respect to the details of the "standard error", an article entitled "Statistics at square One" written by T. D. V. Swinscow, published by British Medical Journal (London, 1980) may be referred to (especially, pages of the article corresponding to pages 28–29 and 36–37 of the Japanese translation thereof).

Then, the second division of the sample of the plant to be examined is left standing while being inoculated with substantially no pathogen, for the above-mentioned predetermined period of time and under the above-mentioned predetermined condition, and the quantity of luminescence from the second division (first reference sample) of the plant to be examined is measured (second step). Here, an average value of the quantities of luminescence from the first reference sample is represented by $C_1$ (counts/sec), and a standard error of the quantities is represented by $m_1$ (counts/sec).

Next, the quantities of the luminescence $S_1$ and $C_1$ measured respectively in the first and second steps are compared with each other. In the present invention, it is preferred to determine whether the plant to be examined has a pathogen resistance or pathogen susceptibility on the basis of the sign (i.e., positive or negative) and/or absolute value of the difference $(S_1-C_1)$ between the above-mentioned $S_1$ and $C_1$.

More specifically, it is preferred that when $S_1>C_1$, the plant to be examined is judged to have pathogen resistance, and when $C_1>S_1$, the plant to be examined is judged to have pathogen susceptibility. In consideration of individual differences among the divisions or samples, and statistical error, it is further preferred that when $(S_1-C_1)\geq\alpha_1$ ($\alpha_1$ is a predetermined value), the plant to be examined is judged to have pathogen resistance, and when $(C_1-S_1)\geq\alpha_2$ ($\alpha_2$ is a predetermined value), the plant to be examined is judged to have pathogen susceptibility. In general, the values $\alpha_1$ and $\alpha_2$ may be determined depending on the kind of a pathogen to be used, and the kind of a plant to be examined. In consideration of measurement error and reproducibility, the above-mentioned values $\alpha_1$ and $\alpha_2$ may preferably be not less than about 30 (counts/sec), more preferably about 50 (counts/sec), in terms of absolute value. On the other hand, the above-mentioned values $\alpha_1$ and $\alpha_2$ may preferably be not less than about 20% (more Preferably not less than about 35%) of the quantity of the luminescence $C_1$ from the first reference sample, in terms of relative value. In a case where a large number of samples of plant (e.g., not less than about 20 samples with respect to one kind of plant) are subjected to measurement, the above-mentioned values $\alpha_1$ and $\alpha_2$ may preferably be determined based on a statistical value (such as average value and standard error).

While the above-mentioned values $\alpha_1$ and $\alpha_2$ can be determined based on an experiment, it is more preferable in view of statistical reproducibility that $\alpha_1=n_1+m_1$, and $\alpha_2=n_1+m_1$. That is, in this embodiment, it is preferred that when $(S_1-C_1)\pm(n_1+m_1)$ is always positive, a plant to be examined is judged to have pathogen resistance, and when $(S_1-C_1)\pm(n_1+m_1)$ is always negative, the plant to be examined is judged to have pathogen susceptibility (third step).

Alternatively, a score of the luminescence is determined according to the following equation, and whether the plant to be examined has pathogen resistance or pathogen susceptibility may be judged depending on the value of the resultant score of luminescence.

Score of luminescence(%)=$\{(S_1-C_1)/C_1\}\times 100$

In the present invention, it is preferred that when the above-mentioned score of luminescence is not less than +20%, more preferably not less than +35% (particularly preferably, not less than +50%), the plant to be examined is judged to have pathogen resistance. On the other hand, it is preferred that when the above-mentioned score of luminescence is not more than −20%, more preferably not more than −35% (particularly preferably, not more than −50%), the plant to be examined is judged to have pathogen susceptibility.

A first embodiment of the apparatus for examining pathogen resistance of a plant according to the present invention has the structure as described above. More specifically, such an apparatus may preferably have the following structure.

The first and second sample positioning means are not particularly restricted as long as they may respectively locate the first division (or first sample) in a position where the first division can be inoculated with a pathogen, and may locate the first and second divisions in predetermined positions where they are left standing. More specifically, the first and second sample positioning means may for example comprise a Petri dish, a preparation glass or another container selected from various types of containers.

The inoculating means is not particularly restricted as long as it can inoculate a pathogen on or into the first division, i.e., as long as it can inoculate a pathogen on or into a plant by various methods such as atomization or spraying, injection and application or coating. More specifically, the inoculating means may preferably comprise an atomizer or sprayer, an injector (e.g., a pipet, syringe), etc.

The sample leaving means is not particularly restricted as long as it can provide an environment in which the second division positioned by the second sample positioning means and the first division positioned by the first sample positioning means and inoculated with a pathogen are left standing under the same conditions for a predetermined period of time. More specifically, for example, the sample leaving means may preferably comprise a device including a dark chamber (or dark box) for the measurement of ultra-weak luminescence, and a environmental condition control device (thermostat and/or humidistat, etc.) for maintaining ambient condition such as temperature and humidity in the dark chamber for a predetermined period of time. This apparatus may further include a gas feeding device for feeding a gas such as air into the dark chamber, as desired.

First and second photodetecting means are not particularly restricted as long as they can measure quantity or amount of ultra-weak luminescence. In view of easiness in measurement, the photodetecting means may preferably comprise a device which is capable of measuring luminescence of not less than about 50 (counts/sec), more preferably not less than about 25 (counts/sec). More specifically, the photodetecting means may for example comprise a photodetecting device such as photomultiplier and CCD.

The examining means is not particularly restricted as long as it can judge whether the above-mentioned value $S_1$ is larger than the value $C_1$ or not, based on those values respectively measured by the first and second photodetecting means. In view of easiness in the measurement for a large number of samples of plant to be examined, and statistical processing of the measurement result, the examining means may preferably comprise a computer. In other words, it is preferred to compare the measured values ($S_1$, $C_1$) with each other by using an electronic computer. More specifically, it is particularly preferred to use an electronic computer which is programmed so as to judge that a plant to be examined has resistance to a pathogen when $(S_1-C_1)\pm(n_1+m_1)$ is always positive, and that the plant to be examined has susceptibility to the pathogen when $(S_1-C_1)\pm(n_1+m_1)$ is always negative.

A second embodiment of the apparatus for examining pathogen resistance of a plant by which pathogen resistance or pathogen susceptibility of a plant is examined has the structure as described above. More specifically, such a second embodiment may preferably have the following structure.

The at least one photodetector to be usable in this second embodiment is not particularly restricted as long as it can measure quantity of ultra-weak luminescence. In view of easiness in measurement, the photodetector may preferably comprise a device which is capable of measuring luminescence of not less than about 50 (counts/sec), more preferably not less than about 25 (counts/sec), similarly as in the above-mentioned first embodiment. More specifically, the photodetector may for example comprise a photodetecting device such as photomultiplier and CCD.

The measuring means to be used in this second embodiment is not particularly restricted as long as it can alternately receive an output of the photodetector in synchronism with switching of the first and second sample positioning means to be opposed to the photodetector, and can measure the quantities of ultra-weak luminescence respectively emitted from the first and second samples. More specifically, the measuring means may preferably comprise a measuring device such as photon counter. In this embodiment, since the measuring means alternately receives an output of the photodetector in synchronism with switching of the first and second sample positioning means to be opposed to the photodetector, the switching of the first and second sample positioning means and/or measuring means may preferably be controlled by an electronic computer so as to conduct such switching quickly and accurately.

In this second embodiment, the first and second sample positioning means, inoculating means, sample leaving means and examining means may preferably be the same as those used in the first embodiment.

The method for evaluating ability of a microbe to be examined (such as non-pathogenic strain and weak-pathogenic strain) to impart pathogen resistance to a plant according to the present invention may preferably be conducted in the following manner.

First, a sample (or a plurality of samples) of a plant to be examined is divided into at least two divisions (i.e., at least two parts of a sample of a plant, or at least two divisions of a plurality of samples of a plant). A microbe to be examined is inoculated on or into one of the at least two divisions (first division). The first division of the sample is left standing for a predetermined period of time and under a predetermined condition which are sufficient for the microbe to react with the first division of the sample, and thereafter the quantity of luminescence (e.g., ultra-weak luminescence) emitted from the first division (second microbe-inoculated sample) of the plant is measured (first step). Here, an average value of the quantities of luminescence from the second microbe-inoculated sample is represented by $S_2$ (counts/sec), and a standard error of the quantities is represented by $n_2$ (counts/sec).

Then, another division of the at least two division (second division) of the sample is left standing while it is not substantially inoculated with the microbe, for the above-mentioned predetermined period of time and under the above-mentioned predetermined condition, and the quantity of luminescence from the second division (second reference sample) of the plant is measured (second step). Here, an average value of the quantities of luminescence from the second reference sample is represented by $C_2$ (counts/sec), and a standard error of the quantities is represented by $m_2$ (counts/sec).

Next, the quantities of the luminescence $S_2$ and $C_2$ measured respectively in the first and second steps are compared with each other. When $S_2>C_2$, the plant is judged to show induced resistance, and when $C_2>S_2$, the plant is judged not to show induced resistance. Here, "induced resistance" refers to a resistance which appears in a plant on the basis of induction by a certain microbe such as pathogen so that the plant has a resistance to another microbe or pathogen (generally speaking, in most cases, the latter microbe has a certain similarity or certain relationship with the former microbe). On the other hand, "pathogen resistance" refers to a property of a plant which is resistant to a certain pathogen.

In consideration of individual differences among the divisions or samples of the plant, and statistical error, it is preferred that when $(S_2-C_2) \geq \beta_1$ ($\beta_1$ is a predetermined value), the plant is judged to have induced resistance, and when $(C_2-S_2) \geq \beta_2$ ($\beta_2$ is a predetermined value), the plant is judged not to have induced resistance. In general, the values $\beta_1$ and $\beta_2$ may be determined depending on the kind of a microbe to be examined, and the kind of a plant to be used. In consideration of measurement error and reproducibility, the above-mentioned values $\beta_1$ and $\beta_2$ may preferably be not less than about 30 (counts/sec), more preferably about 50 (counts/sec), in terms of absolute value. On the other hand, the above-mentioned values $\beta_1$ and $\beta_2$ may preferably be not less than about 20% (more preferably not less than about 35%) of the quantity of the luminescence $C_2$ from the second reference sample, in terms of relative value. In a case where a large number of samples of plant (e.g., not less than about 20 samples with respect to one kind of plant) are subjected to measurement, the above-mentioned values $\beta_1$ and $\beta_2$ may preferably be determined based on a statistical value (such as average value and standard error).

While the above-mentioned values $\beta_1$ and $\beta_2$ can be determined based on an experiment, it is more preferable in view of statistical reproducibility that $\beta_1 = n_2 + m_2$, and $\beta_2 = n_2 + m_2$. That is, in this embodiment, it is preferred that when $(S_2 - C_2) \pm (n_2 + m_2)$ is always positive, the plant is judged to have induced resistance, and when $(S_2 - C_2) \pm (n_2 + m_2)$ is always negative, the plant is judged not to have induced resistance (third step).

A first embodiment of the apparatus for evaluating the ability of a microbe (such as non-pathogenic strain and weak-pathogenic strain) to be examined to impart pathogen resistance to a plant according to the present invention has the structure as described above. More specifically, such an apparatus may preferably have the following structure.

The evaluating means is not particularly restricted as long as it can judge whether the above-mentioned value $S_2$ is larger than the value $C_2$ or not, based on those values respectively measured by the first and second photodetecting means. In view of easiness in the measurement for a large number of samples of plant, and statistical processing of the measurement result, the evaluating means may preferably comprise a computer. In other words, it is preferred to compare the measured values ($S_2$ and $C_2$) with each other by using an electronic computer. More specifically, it is particularly preferred to use an electronic computer which is programmed so as to judge that the plant has induced resistance to a pathogen when $(S_2 - C_2) \pm (n_2 + m_2)$ is always positive, and that the plant does not have induced resistance to the pathogen when $(S_2 - C_2) \pm (n_2 + m_2)$ is always negative.

In this embodiment, the first and second sample positioning means, inoculating means, sample leaving means, and first and second photodetecting means may preferably be the same as those used in the first embodiment of the apparatus for examining pathogen resistance of a plant as described hereinabove.

A second embodiment of the apparatus for evaluating the ability of a microbe (such as non-pathogenic strain and weak-pathogenic strain) to be examined to impart pathogen resistance to a plant according to the present invention has the structure as described above. More specifically, such an apparatus may preferably have the following structure.

In this second embodiment, the first and second sample positioning means, inoculating means, sample leaving means, and at least one photodetector may preferably be the same as those used in the second embodiment of the apparatus for examining pathogen resistance of a plant as described hereinabove. In addition, the evaluating means in this second embodiment may preferably be the same as that used in the first embodiment of the apparatus for examining pathogen resistance of a plant as described hereinabove.

The method for evaluating the ability of an agricultural chemical to activate pathogen resistance of a plant according to the present invention may preferably be conducted in the following manner.

First, a sample (or a plurality of samples) of a plant is divided into at least two divisions (i.e., at least two parts of a sample of a plant, or at least two divisions of a plurality of samples of a plant). One division of the at least two divisions (first division) of the sample is caused to absorb an agricultural chemical to be examined, and is left standing under a predetermined condition and for a predetermined period of time which allow the agricultural chemical to be sufficiently absorbed into the first division. Then, a pathogen is inoculated on or into the first division, and the first division is left standing under a predetermined condition and for a predetermined period of time which are sufficient for the pathogen to react with the first division. Thereafter, the quantity of ultra-weak luminescence emitted from the first division (agricultural chemical-absorbing plant) is measured (first step). Here, an average value (counts/sec) of the quantities of ultra-weak luminescence emitted from the agricultural chemical-absorbing plant is represented by $S_3$, and a standard error of such quantities is represented by $n_3$ (counts/sec).

On the other hand, another division of the at least two divisions (second division) of the sample is not caused to absorb the agricultural chemical to be examined, and is left standing under a predetermined condition and for a predetermined period of time so that the second division is subjected to the same condition as that for the first division (agricultural chemical-absorbing plant). Then, a pathogen is inoculated on or into the second division, and the second division is left standing under a predetermined condition and for a predetermined period of time which are sufficient for the pathogen to react with the second division. Thereafter, the quantity of ultra-weak luminescence emitted from the second division (third reference sample) is measured (second step). Here, an average value (counts/sec) of the quantities of ultra-weak luminescence emitted from the third reference sample is represented by $C_3$, and a standard error of such quantities is represented by $m_3$ (counts/sec).

Next, the quantities of ultra-weak luminescence $S_3$ and $C_3$ respectively measured in the first and second steps are compared with each other. As the value $S_3$ is remote from the value $C_3$ (i.e., the absolute value of $|S_3 - C_3|$ is larger), the agricultural chemical is evaluated to have activated pathogen resistance of the plant to a larger extent. On the other hand, as the value $S_3$ is near to the value $C_3$ (i.e., the absolute value of $|S_3 - C_3|$ is smaller), the agricultural chemical is evaluated not to be suitable for activation of the pathogen resistance of the plant. In a case where a large number of samples of a plant are subjected to such measurement, when individual differences among the samples, and statistical error are considered, it is further preferred to consider the standard errors $n_3$ and $m_3$ in view of statistical reproducibility. That is, it is preferred in this embodiment that as the value of $S_3 \pm n_3$ of the plant is remoter from the value of $C_3 \pm m_3$ (that is, as the absolute value of $|(S_3 \pm n_3) - (C_3 \pm m_3)|$ is larger), the agricultural chemical is judged to have activated pathogen resistance of the plant to a larger extent, and as the value of $S_3 \pm n_3$ is nearer to the value of $C_3 \pm m_3$ (i.e., the absolute of $|(S_3 \pm n_3) - (C_3 \pm m_3)|$ is smaller), the agricultural chemical is evaluated not to be suitable to activate pathogen resistance of the plant (third step 3).

A first embodiment of the apparatus for evaluating the ability of an agricultural chemical to activate pathogen resistance of a plant according to the present invention has the structure as described above. More specifically, such an apparatus may preferably have the following structure.

The absorbing means is not particularly restricted as long as it can cause the first division of sample to absorb an agricultural chemical. More specifically, the absorbing means may preferably comprise a device which is capable of causing the first division of sample to absorb an agricultural chemical by an appropriate method such as atomization or spraying, injection and application or coating. For example, the absorbing means may comprise a device such as atomizer or sprayer and injector (inclusive of a pipet, a syringe, etc.).

The evaluating means is not particularly restricted as long as it can judge whether the value $S_3$ is larger than the value $C_3$ or not, based on those values measured by the first and second photodetecting means. In view of the easiness in the measurement of a large number of samples of plant, and statistical processing of the measurement result, the evaluating means may preferably comprise a computer. In other words, it is preferred to compare the measured values $S_3$ and $C_3$ with each other by using an electronic computer. It is particularly preferred to use an electronic computer which is programmed so as to evaluate that the agricultural chemical has activated pathogen resistance of the plant to a larger extent as the value of $S_3 \pm m_3$ is remoter from the value of $C_3 \pm m_3$ (i.e., the absolute value of $|(S_3 \pm n_3)-(C_3 \pm m_3)|$ is larger), and to evaluate that the agricultural chemical is not suitable to activate pathogen resistance of the plant chemical as the value of $S_3 \pm n_3$ is nearer to the value of $C_3 \pm m_3$ (i.e., the absolute value of $|(S_3 \pm n_3)-(C_3 \pm m_3)|$ is smaller).

The above-mentioned first embodiment of the apparatus for evaluating the ability of an agricultural chemical to impart pathogen resistance to a plant may preferably include: first and second sample positioning means, first and second sample leaving means, inoculating means, and first and second photodetecting means which are the same as those constituting the first embodiment of the apparatus for examining pathogen resistance of a plant as described hereinabove.

A second embodiment of the apparatus for evaluating the ability of an agricultural chemical to impart pathogen resistance to a plant has the structure as described hereinabove. More specifically, such a second embodiment may preferably have the following structure.

That is, the second embodiment of the apparatus for evaluating the ability of an agricultural chemical may preferably include: first and second sample positioning means, first and second sample leaving means, inoculating means, at least one photodetector, and measuring means, which are the same as those constituting the second embodiment of the apparatus for examining pathogen resistance of a plant as described hereinabove. In addition, the second embodiment of the apparatus for evaluating the ability of an agricultural chemical may preferably include absorbing means and evaluating means which are the same as those constituting the first embodiment of the apparatus for evaluating the ability of an agricultural chemical to impart pathogen resistance to a plant as described hereinabove.

Hereinbelow, preferred embodiments of the present invention will be described in further detail with reference to accompanying drawings. Common members or elements shown in the drawings are denoted by common reference numerals and repetitive explanations thereof are omitted in the description appearing hereinbelow.

With reference to FIG. 1, an apparatus for examining pathogen resistance of a plant according to a first embodiment of the present invention will be described.

The above-mentioned apparatus according to the first embodiment comprises: an ultra-weak luminescence detector 20 including two photomultipliers (hereinafter, referred to as "PMT"), photon counters 30 connected to the respective PMTs 10, an electronic computer 40 for receiving a digital signal from the photon counters 30, and an electric power source (not shown) for supplying electric power to the PMTs 10 and the photon counters 30 (in this embodiment, the power sources are built in the photon counters 30).

As shown in FIG. 1, the ultra-weak luminescence detector 20 includes a laterally L-shaped casing 21, the PMTs 10 respectively disposed in two housings 22 provided upright on the inside of the ceiling of a projection of the casing 21, two sprayers (or atomizers) 50 provided on the upper surface of the left horizontal part of the casing 21 at predetermined positions, and sample conveying mechanism provided on the inside bottom of the casing 21. The PMTs 10 in the housings 22 are disposed with their detecting portions faced downward. The sprayers 50 and the PMTs 10 are arranged in a direction of the movement of a sliding member (or slide body) 61 as shown in FIG. 1. The PMT 10 comprises an electron tube for detecting ultra-weak luminescence in a range of from UV radiation to infrared radiation (preferably about 200 nm–1700 nm, more preferably about 200 nm–900 nm). In this embodiment, each PMT 10 comprises an electron multiplier disposed between a photocathode surface and an anode of a photoelectric tube so that it can detect even weakest light. In this embodiment, a photomultiplier R208 (mfd. by Hamamatsu Photonics K.K.) is used as the PMT 10.

The housing 22 is formed of a material (such as aluminum) which can completely shield the housing 22 from any external light, and each housing 22 has an electrically-driven openable shutter (not shown) at the bottom thereof. A shielding film or sheet 90 of rubber is provided at a lower housing part between the housings 22 for the purpose of preventing the intrusion of luminescence from the adjacent Petri dish. The casing 21 is formed of a material which can completely shield the casing 21 from any external light. In the left side surface of the casing 21, there is provided an openable door (not shown) for introducing and taking out a sample. A seal is provided in a gap or clearance between the casing 21 and the door so that any external light cannot enter the inside of the casing when the door is closed. Each sprayer 50 includes a liquid reservoir layer (not shown), and spraying rate (or spraying amount)—adjusting means (not shown) which is controlled by the electronic computer 40.

The sample conveying mechanism comprises the sliding member 61, a feed screw 62 for horizontally moving the sliding member 61, supporting rods 63 passing horizontally through the lateral end portions of the sliding member 61 so as to support the sliding member 61, and a motor (not shown) and a gear mechanism (not shown) for rotating the feed screw 62. The motor and gear mechanism (not shown) are accommodated in the housing 22. The housing 22 also functions to support the feed screw 62 and the supporting rods 63. The motor is controlled by the electronic computer 40. A stage 70 is fixed to the upper surface of the sliding member 61. The upper surface of the stage 70 functions as a sample mount at which the sample is to be positioned.

The photon counter 30 counts the number of photons detected by the PMT 10 to measure the quantity of luminescence or light emitted from the sample. In this embodiment, the photon counter 30 comprises, e.g., a photon counter C1230 (or C767) mfd. by Hamamatsu Photonics k.k. In a case where a photon counter 30 with a built-in high-voltage stabilized DC power source (such as photon counter C1230 used in this embodiment) is used, it is not necessary to specially provide another power source.

The electronic commuter 40 may for example comprise a desk-top type personal computer. In this embodiment, e.g., a PC-9800 type personal computer (mfd. by NEC, i.e., Nippon Electric Co., Ltd.) is used as the computer 40. While the above-mentioned PMTs 10 are used as the photoelectron multipliers in this embodiment, another device may also be used as long as the device can conduct high-susceptibility photodetection in the visible radiation range and/or the near infrared radiation range (about 200 nm–1700 nm). Such a device may for example comprise a detecting device or element of high susceptibility, such as image intensifier and avalanche photodiode.

In this embodiment, it is also possible to provide an optical fiber right under the photocathode surface of the PMT so that so that the optical fiber is located between the PMT 10 and the sample to be measured, whereby the luminescence emitted from the sample is transmitted to the photomultiplier through the optical fiber.

Figure 2:
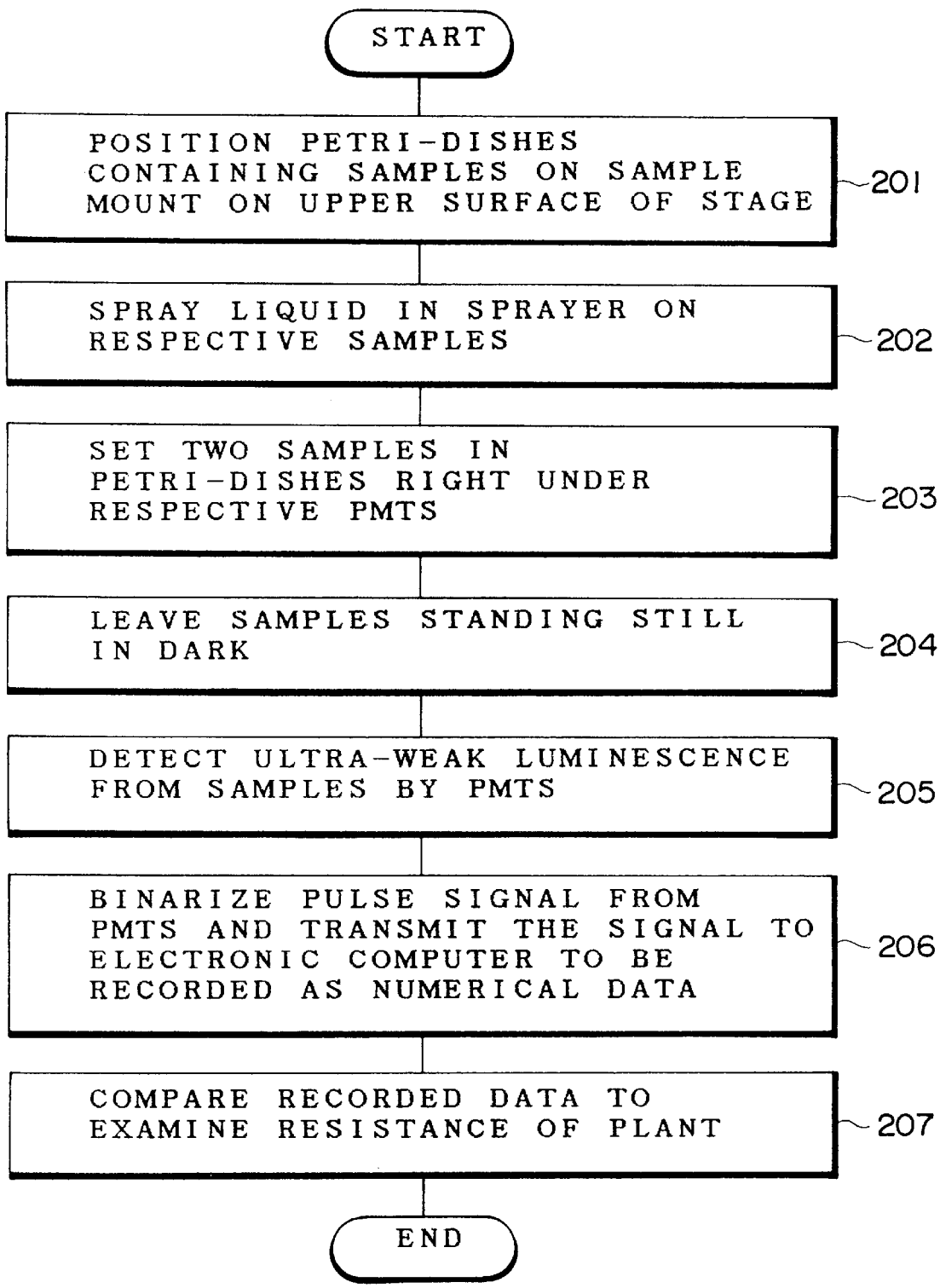
FIG. 2 is a flow chart for illustrating an examination method according to a first embodiment of the present invention.

Next, the method for examining pathogen resistance of a plant according to a first embodiment of the present invention will be explained with reference to a flow chart of FIG. 2.

First, plant seed to be examined (hereinafter, referred to as "sample") is accommodated in two Petri dishes 81 and 82 which have been prepared beforehand. The Petri dishes 81 and 82 respectively accommodating the samples are positioned on the sample mount which is the upper surface of the stage 70 provided in the ultra-weak luminescence detector 20 (Step 201). At this time, the samples are introduced into the ultra-weak luminescence detector 20 through the door thereof. After the Petri dishes 81 and 82 are set on the upper surface of the stage 70, the door is perfectly closed so that no external light enters the inside of the detector 20.

Then, liquids contained in the sprayers 50 is sprayed on the respective samples (Step 202). One of the sprayers 50 disposed on the upper surface of the ultra-weak luminescence detector 20, contain an aqueous solution containing a pathogen (hereinafter, referred to as "aqueous pathogen solution"), and the other of the sprayers 50 contains distilled water. Either of the sprayers 50 may contain the aqueous pathogen solution or distilled water. In this first embodiment of the present inventions the upper left sprayer 50 shown in FIG. 1 contains the aqueous pathogen solution, and the lower right sprayer 50 contains distilled water.

Accordingly, when the aqueous pathogen solution is sprayed on one of the samples, distilled water is sprayed on the other of the samples. As a result, a sample to be examined, i.e., a sample inoculated with the pathogen (hereinafter, referred to as "pathogen-inoculated sample) and a sample inoculated with substantially no pathogen (hereinafter, referred to as "reference sample") are prepared.

Then, the feed screw 62 of the sample conveying mechanism is rotated to move the sliding member 61 (located at an upper left side in FIG. 1) to a lower right side in FIG. 1, so that the two samples in the Petri dishes 81 and 82 are positioned right under the photomultipliers respectively corresponding to the Petri dishes 81 and 82 (Step 203). This movement is conducted in accordance with a command or instruction from the electronic computer 40.

Next, for a certain period of time, the quantity of luminescence from the samples is not measured and the samples are left standing still in dark (Step 204). At this time, since the interior of the ultra-weak luminescence detector 20 is completely shielded from external light and the interior of the detector 20 may function as a dark chamber, the samples can be left standing still in dark as they are. The period of time during which the samples are left standing still may usually be about 1 hour to 5 days. Most of samples may suitably be left standing still for about 1 to 3 days, while such a standing period of time may be intrinsically determined depending on the kind of a plant to be used. Accordingly, it is preferred to collect data on this period in advance by a preparatory experiment as described below. Once such data are collected in this manner, the resultant data may be used repeatedly in examinations or experiments to be conducted later.

Then, the shutters (not shown) of the housings 22 are opened in response to an instruction from the electronic computer 40 to detect ultra-weak luminescence from the respective samples 80 by the corresponding PMTs 10 (step 205). In this embodiment, the period of time for the measurement by the PMTs is 1 minute. The PMTs comprise, e.g., photomultipliers R208 mfd. by Hamamatsu Photonics K. K. The Photomultipliers may be operated under conditions including: an applied voltage of +1000 V, a lower discrimination level of 0.90, an upper discrimination level of 9.99 and a gate time of 1 second. The above-mentioned PMT 10 shows, e.g., a dark counter of about 20 (counts/sec).

Then, pulse signals from the respective PMTs 10 are binarized by the corresponding photon counters 30 and are transmitted to the electronic computer 40 to be recorded therein as numerical data (Step 206).

Then, Steps 203 to 206 are repeated so as to obtain a predetermined quantity of data suitable for the examination to be conducted.

Next, in the electronic computer 40, the recorded data are compared with each other to examine pathogen resistance of the plant (Step 207). More specifically, This examination may be conducted in the following manner.

Thus, an average value of data obtained from the reference sample is represented by C (counts/sec), and a standard error of such data is represented by m (counts/sec). On the other hand, an average value of data obtained from the pathogen-inoculated sample is represented by S (counts/sec), and a standard error of such data is represented by n (counts/sec). In this embodiment, the electronic computer 40 is programmed so that the plant to be examined is judged to have resistance to the pathogen when $(S-C)\pm(n+m)$ is always positive, and the plant is judged to have susceptibility to the pathogen when $(S-C)\pm(n+m)$ is always negative. In this embodiment, the thus obtained examination results are displayed on a monitor connected to the computer 40.

In the examination method according to this embodiment, one examination apparatus is used, samples to be loaded into the examination apparatus are sequentially replaced, and the same examination is repeated to collect predetermined data to be used for the examination. However, it is also possible to use a plurality of examination apparatuses connected to the electronic computer 40 so as to collect the data for examination at once. Whichever method is used, it is possible to conduct the examination in a much shorter period of time as compared with that required for the conventional examination method. For example, when tomato is used as a plant to be examined, the conventional examination method requires a period of one to two months at the shortest. On the other hand, when the above-mentioned examination method according to the present invention is used, the preparation of a sample may take a period of one to two days, for example, and the measurement per se may take only a time of several minutes, for example.

The examination method according to the present invention may also be conducted by using as an apparatus for examining pathogen resistance of a plant according to a second embodiment as described later. In a case where the apparatus according to the second embodiment is used, the method according to the first embodiment can be conducted by using the same procedure as that according to the second embodiment as described later.

Figure 3:
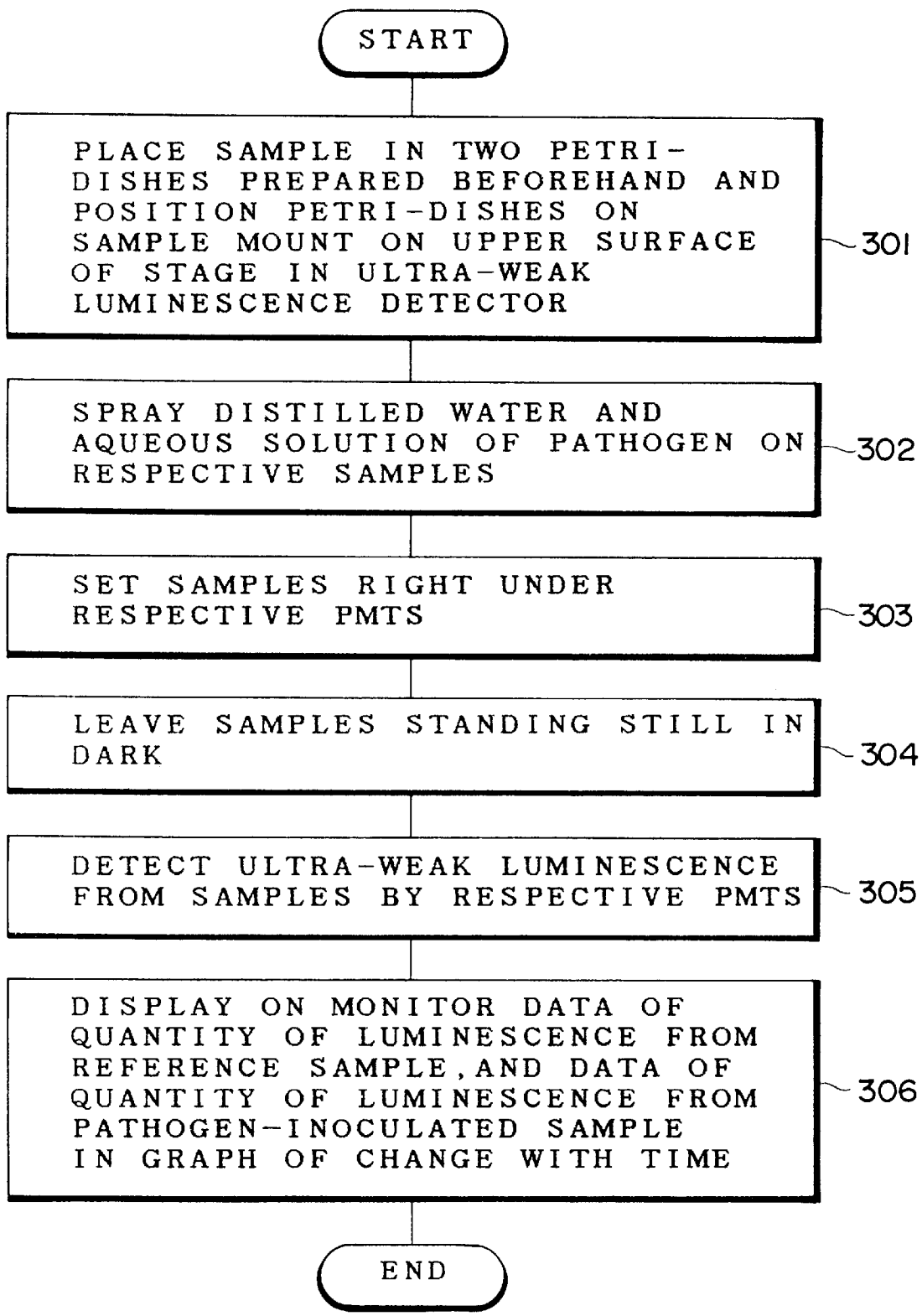
FIG. 3 is a flow chart of a preparatory experiment to be conducted as desired in the examination method according to the first embodiment of the present invention.

Next, with reference to a flow chart of FIG. 3, there is described a preparatory experiment for determining a still-standing period of time counted from the inoculation of a pathogen into a plant to the start of the measurement of luminescence quantity. Such a preparatory experiment may be conducted as desired, when the pathogen resistance of a plant is to be examined according to the present invention. As described above, samples of plant of one kind may have the same still-standing period of time for the measurement of luminescence quantity. Accordingly, once data on the still-standing period of time is obtained, it can be repeatedly used in the examination of samples of the same kind.

First, in the same manner as in the above-mentioned examination method according to the first embodiment, samples are accommodated in two Petri dishes which have been prepared beforehand, and the Petri dishes are positioned on the sample mount which is the upper surface of the stage 70 provided in the ultra-weak luminescence detector 20 (Step 301).

Then, in the same manner as in the examination method according to the first embodiment, two liquids contained in the sprayers 50 are sprayed on the respective samples (Step 302). Thus, a pathogen-inoculated sample and a reference sample are prepared.

Then, the feed screw 62 of the sample conveying mechanism is rotated to move the sliding member 61 to a predetermined position so that the two samples contained in the Petri dishes disposed on the stage 70 are positioned right under the photomultipliers respectively corresponding to the Petri dishes (Step 303). This movement is conducted in accordance with an instruction from the electronic computer 40.

Next, the samples are left standing still in dark for about 1 hour (Step 304). During such a period of time, quantity of luminescence from the samples is not measured.

Then, the shutters (not shown) of the housings 22 are opened in response to an instruction from the electronic computer 40 so as to detect ultra-weak luminescence emitted from the respective samples by the corresponding PMTs 10 (Step 305). Such detection is conducted for a period of time of about 3 to 4 days, for example. Pulse signals from the respective PMTs 10 are digitized by the corresponding photon counters 30 and are transmitted to the electronic computer 40 to be recorded as numerical data indicating a change in the quantity of luminescence with the elapse of time.

Next, the data on the quantity of luminescence from the reference sample, and the data on the quantity of luminescence from the pathogen-inoculated sample are graphed to provide a curve showing a change with the elapse of time, and the resultant graph is displayed on the monitor (Step 306). Subtraction values are read from the curves showing a change with time in the displayed graph, thereby to determine a still-standing period of time (i.e., a period of time counted from the inoculation of a pathogen to the start of the measurement) which is most suitable for the provision of optimum measurement result.

Next, some examples of the above-mentioned examination using this apparatus will be described.

In a first example of the examination, tomato was used as a plant to be examined The varieties of the tomatoes used in this example were three, i.e., LS-89, Okitsu BF-101, and Ponterosa. As pathogens, typical fungi inclusive of wilt pathogen (or a pathogen of wilt disease) (*Fusarium oxysporum* f. sp. Lycoperisici Race 1) and wilt pathogen (*Fusarium oxysporum* f. sp. Lycoperisici Race 2) were used. Further, as non-pathogenic microbe for imparting induced resistance to a plant (hereinafter, simply referred to as "non-pathogenic microbe"), *Fusarium oxysporum* S-160 (hereinafter, referred to as "S-160") which is in close relation with the wilt pathogen was used. It is widely known that the tomato LS-89 exhibits resistance to the wilt pathogen (Race 1), and exhibits intermediate reactivity between resistance and susceptibility to the wilt pathogen (Race 2) according to a conventional method wherein a pathogen is first inoculated into a plant to be examined, and thereafter, various symptoms caused in the plant by the above-mentioned inoculation (e.g., putrefaction, rotting, spots, blight, wilting, etc.) are observed to examine the pathogen resistance and pathogen susceptibility of the plant (in the description of Examples appearing hereinafter, such an intermediate reactivity is referred to as "tolerance"). In a case where the above-mentioned conventional method is used, it is also widely known that the tomato Okitsu BF-101 exhibits resistance to the wilt pathogen (Race 1), and exhibits susceptibility reaction to the wilt pathogen (Race 2). It is widely known that tomato Ponterosa exhibits susceptibility reaction to both of the wilt pathogen (Race 1) and wilt pathogen (Race 2) (see "Sakata's Catalogue of Vegetables", 1991–1992, page 180, published by "Sakata-No-Tane" K.K.).

Then, the examination method used in this Example will be described.

First, on Aug. 31, 1992, seeds of the above-mentioned respective varieties were sowed in a medium contained in Petri dishes 70.

On Sep. 1, 1992, culture media (or culture solutions) respectively containing the above-mentioned kinds of pathogens each in a spore concentration of about $10^7$ spores/ml (each in an amount of 2 ml) were inoculated on germinated seeds of the above-mentioned respective varieties. As a result, totally 12 kinds of samples (inclusive of non-inoculated samples) were prepared. The pathogens to be used for the inoculation were subjected to shaking culture on a PD (potato dextrose) medium for 3 days at 25° C.

Then, on Sep. 2, 1992 (after about 16 hours counted from the inoculation of the pathogen), the germinated seeds of the respective varieties were examined by using the above-mentioned apparatus according to this embodiment. The examination method was conducted in a manner as described hereinabove.

The examination results are shown in the following Table 1.

TABLE 1

| No. | Variety | Pathogen | Measured value (CPS) | Difference with non-inoculated sample (CPS) | Reduction of variety |
|---|---|---|---|---|---|
| 1 | LS-89 | Non-inoculated | 111 ± 1.6 (N = 100) | — | |
| 2 | LS-89 | Pathogen (Race 1) | 245 ± 2.8 (N = 100) | 134 ± 4.4 > 0 | resistance |
| 3 | LS-89 | Pathogen (Race 2) | 131 ± 2.0 (N = 100) | 20 ± 3.6 | tolerance |

TABLE 1-continued

| No. | Variety | Pathogen | Measured value (CPS) | Difference with non-inoculated sample (CPS) | Reduction of variety |
|---|---|---|---|---|---|
| 4 | LS-89 | S-160 | 230 ± 3.9 (N = 100) | 119 ± 5.5 > 0 | induced resistance |
| 5 | Okitsu BF-101 | Non-inoculated | 140 ± 2.2 (N = 100) | — | |
| 6 | Okitsu BF-101 | Pathogen (Race 1) | 166 ± 3.0 (N = 100) | 26 ± 5.2 | (resistance) |
| 7 | Okitsu BF-101 | Pathogen (Race 2) | 106 ± 1.2 (N = 100) | −34 ± 3.3 < 0 | susceptibility |
| 8 | Okitsu BF-101 | S-160 | 260 ± 4.1 (N = 100) | 120 ± 6.3 > 0 | induced resistance |
| 9 | Ponterosa | Non-inoculated | 249 ± 2.1 (N = 100) | — | |
| 10 | Ponterosa | Pathogen (Race 1) | 240 ± 1.8 (N = 100) | −9 ± 3.9 | (susceptibility) |
| 11 | Ponterosa | Pathogen (Race 2) | 166 ± 2.3 (N = 100) | −83 ± 4.4 < 0 | susceptibility |
| 12 | Ponterosa | S-160 | 309 ± 4.7 (N = 100) | 60 ± 6.8 | (induced resistance) |

As shown in the above Table 1, according to the judgement by the above-mentioned apparatus, the tomato LS-89 exhibited resistance to the wilt pathogen (Race 1), and exhibited susceptibility to the wilt pathogen (Race 2). Okitsu BF-101 exhibited resistance to the wilt pathogen (Race 1) and exhibited susceptibility to the wilt pathogen (Race 2). Ponterosa exhibited susceptibility to both of the wilt pathogen (Race 1) and the wilt pathogen (Race 2). These results are consistent with (or correspond to) those generally known in the art as described above. Accordingly, it has been found that the above-described method using the above apparatus according to the present invention is very effective to examine the resistance or susceptibility of a plant.

In addition, according to the judgement by the above-mentioned apparatus, it has been found that S-160 imparted "induced resistance" to any of the varieties used in this Example.

Further, when a difference between the pathogen-inoculated sample and the reference sample is displayed on the monitor as in the above Example, such displaying is very useful for the judgement of the strength of the induced resistance.

As described above, when the examination is conducted by use of the above-mentioned apparatus or the above-mentioned method using such an apparatus, the pathogen resistance or pathogen susceptibility can be examined easily and accurately.

Next, a second example of the examination using cabbage will be described.

The varieties used in this Example were two varieties inclusive of Akiwase, and YR Kinshu-Kyoryoku 152. The pathogens used in this Example were a bacterium *Erwina carotovora* subsp. *carotovora* capable of causing soft rot disease, and a bacterium *Xanthomonas campestris* pv. *campestris* capable of causing black rot disease. In a case where the above-mentioned conventional method is used, it is also widely known that Akiwase exhibits tolerance to the soft rot disease and resistance to the black rot disease (see "Masuda no Tane" General Catalogue, 1991–1992, pages. 6–10, published by Masuda Saishujo K.K.). It is widely known that YR Kinshu-Kyoryoku 152 exhibits resistance to the soft rot disease.

The examination method used in this Example will be described.

On Aug. 31, 1992, seeds of the above-described varieties were sowed on a medium contained in Petri dishes 70.

On Sep. 1, 1992, the above-described bacteria were inoculated into germinated seeds of the above-mentioned respective varieties. As a result, totally five kinds of samples (inclusive of non-inoculated samples) to be examined were prepared.

On Sep. 2, 1992 (after about 16 hours counted from the inoculation of the bacteria), the germinated seeds of the respective varieties were examined by using the apparatus according to this embodiment. The examination method was the same as that described hereinabove.

The examination results are shown in the following Table 2.

TABLE 2

| No. | Variety | Pathogen (Bacteria) | Measured value (CPS) | Difference with non-inoculated sample (CPS) | Reaction of variety |
|---|---|---|---|---|---|
| 1 | Akiwase | Non-inoculated | 196 ± 1.4 (N = 100) | — | |
| 2 | Akiwase | Soft rot | 275 ± 1.8 (N = 100) | 79 ± 3.2 > 0 | tolerance |
| 3 | Akiwase | Black rot | 307 ± 5.0 (N = 100) | 111 ± 6.4 > 0 | resistance |
| 4 | YR Kinshu Kyoryoku 152 | Non-inoculated | 128 ± 1.2 (N = 100) | — | |
| 5 | YR Kinshu Kyoryoku 152 | Soft rot | 289 ± 3.4 (N = 100) | 161 ± 4.6 > 0 | resistance |

As shown in the above Table 2, according to the judgement by this apparatus, Akiwase exhibited tolerance to the pathogen of soft rot disease and exhibited resistance to the pathogen of black rot disease. YR Kinshu-Kyoryoku 152 exhibited resistance to the pathogen of soft rot disease.

These results are consistent with those generally known in the art as described above. Thus, it has been found that the apparatus according to this embodiment and the above-described method using such an apparatus are very effective when a variety of a plant having resistance to bacterium is to be examined.

Next, a third example using a rice plant will be described.

The varieties of rice plant used in this Example were two inclusive of Aichi-Asahi and Kogane-Bare. The pathogens used in this Example were a rice blast fungus *Pyricularia*

*oryzae* Cavara strain 23-02, and a rice blast fungus strain 23-03. In a case where the above-mentioned conventional method is used, it has been confirmed that Aichi-Asahi exhibits compatibility (susceptibility) to a rice blast fungus. On the other hand, in a case where the above-mentioned conventional method is used, it has also been confirmed that Kogane-Bare is a variety to which incompatibility (resistance) has been imparted.

Next, the examination method used in this Example will be described.

On Aug. 31, 1992, seeds of the above-described varieties were sowed on a medium contained in Petri dishes 70.

On Sep. 1, 1992, the above-described pathogens were respectively inoculated on germinated seeds of the above-mentioned varieties. As a result, totally six kinds of samples (inclusive of non-inoculated samples) were prepared.

On Sep. 2, 1992 (after about 16 hours counted from the inoculation of the pathogen), the germinated seeds of the above-mentioned respective varieties were examined by using the apparatus according to this embodiment. The examination method used in this Example was the same as described hereinabove.

The examination results are shown in the following Table 3.

TABLE 3

| No. | Variety | Pathogen | Measured value (CPS) | Difference with non-inoculated sample | Reaction of variety |
|---|---|---|---|---|---|
| 1 | Aichi-Asahi | Non-inoculated | 410 ± 5.3 (N = 100) | — | |
| 2 | Aichi-Asahi | Rice blast 23-02 | 263 ± 3.5 (N = 100) | −146 ± 8.8 < 0 | compatibility |
| 3 | Aichi-Asahi | Rice blast 23-03 | 296 ± 4.4 (N = 100) | −114 ± 9.7 < 0 | compatibility |
| 4 | Kogane-Bare | Non-inoculated | 380 ± 5.2 (N = 100) | — | |
| 5 | Kogane-Bare | Rice blast 23-02 | 474 ± 7.2 (N = 100) | 94 ± 12.4 | (incompatibility) |
| 6 | Kogane-Bare | Rice blast 23-03 | 298 ± 4.1 (N = 100 | −82 ± 9.3 | (compatibility) |

As shown in the above Table 3, according to the judgement by this apparatus, Aichi-Asahi exhibited compatibility to the rice blast fungus, and Kogane-Bare exhibited incompatibility to the rice blast fungus 23-02. These results are consistent with those generally known in the art as described above. Thus, it has been found that even a slight difference in specificity between the respective varieties with respect to a pathogen may be examined by use of the apparatus according to this embodiment.

Next, an apparatus for evaluating the ability of a microbe to impart pathogen resistance to a plant according to a second embodiment of the present invention will be described with reference to FIG. 4.

Basic differences between the apparatus according to the second embodiment and that according to the first embodiment are in the number of the photomultiplier 10, and in the structure of the stage 70. That is, two photomultipliers 10 are provided in the first embodiment, while one photomultiplier 10 is provided in the second embodiment. In this embodiment, the stage 70 includes a sliding member fixing portion 71 and a stage body 72. The stage body 72 is supported by a supporting mechanism 73 disposed on the sliding member fixing portion 71. The stage body 72 may be horizontally reciprocated by a motor (not shown) disposed at a substantially middle part of the sliding member fixing portion 71, and a reciprocating mechanism (not shown). The motor is controlled by an electronic computer 40. The stage body 72 is repeatedly reciprocated every about 5 seconds in response to an instruction from the electronic computer 40 to be displaced to a predetermined position, so that luminescence emitted from samples contained in two Petri dishes 81 and 82 can be alternately detected by one photomultiplier 10. In this embodiment, since only one photomultiplier 10 is provided, the number of the photon counter 30 may be one.

The quantities of the luminescence thus detected are processed to be compared with each other by the electronic computer 40 in the same manner as in the first embodiment.

Next, the method for examining pathogen resistance of a plant according to a second embodiment will be described.

First, seed of a plant to be examined (hereinafter, referred to as "seed") is accommodated in two Petri dishes 81 and 82 which have been prepared beforehand. The Petri dishes 81 and 82 containing the seed are placed on the sample mount which is the upper surface of the stage 70 provided in the ultra-weak luminescence detector 20. The seed is introduced into the ultra-weak luminescence detector 20 through the door of the detector 20. After the Petri dishes 81 and 82 have been set on the upper surface of the stage 70, the door is perfectly closed so as to shield the interior of the detector 20 from any external light.

Then, liquids contained in sprayers 50 are respectively sprayed on the seed contained in the Petri dishes 81 and 82. One of the sprayers 50 disposed on the upper surface of the ultra-weak luminescence detector 20, contains an aqueous solution containing a bacterium to be examined (hereinafter, referred to as "aqueous bacterial suspension"), and the other of the sprayers 50 contains distilled water. While either one of the sprayers 50 may contain the aqueous bacterial suspension or distilled water, in this second embodiment, the upper left sprayer 50 in FIG. 4 contains the aqueous bacterial suspension, and the lower right sprayer 50 contains distilled water.

Accordingly, when the aqueous bacterial suspension is sprayed on the seed contained in one sprayer 50, distilled water is sprayed on the seed contained in the other sprayer 50. As a result, seed to be examined, i.e., seed inoculated with the bacterium to be detected (hereinafter, referred to as "microbe-inoculated seed"), and seed not inoculated with the bacterium (hereinafter, referred to as "reference seed") are prepared.

Figure 4:
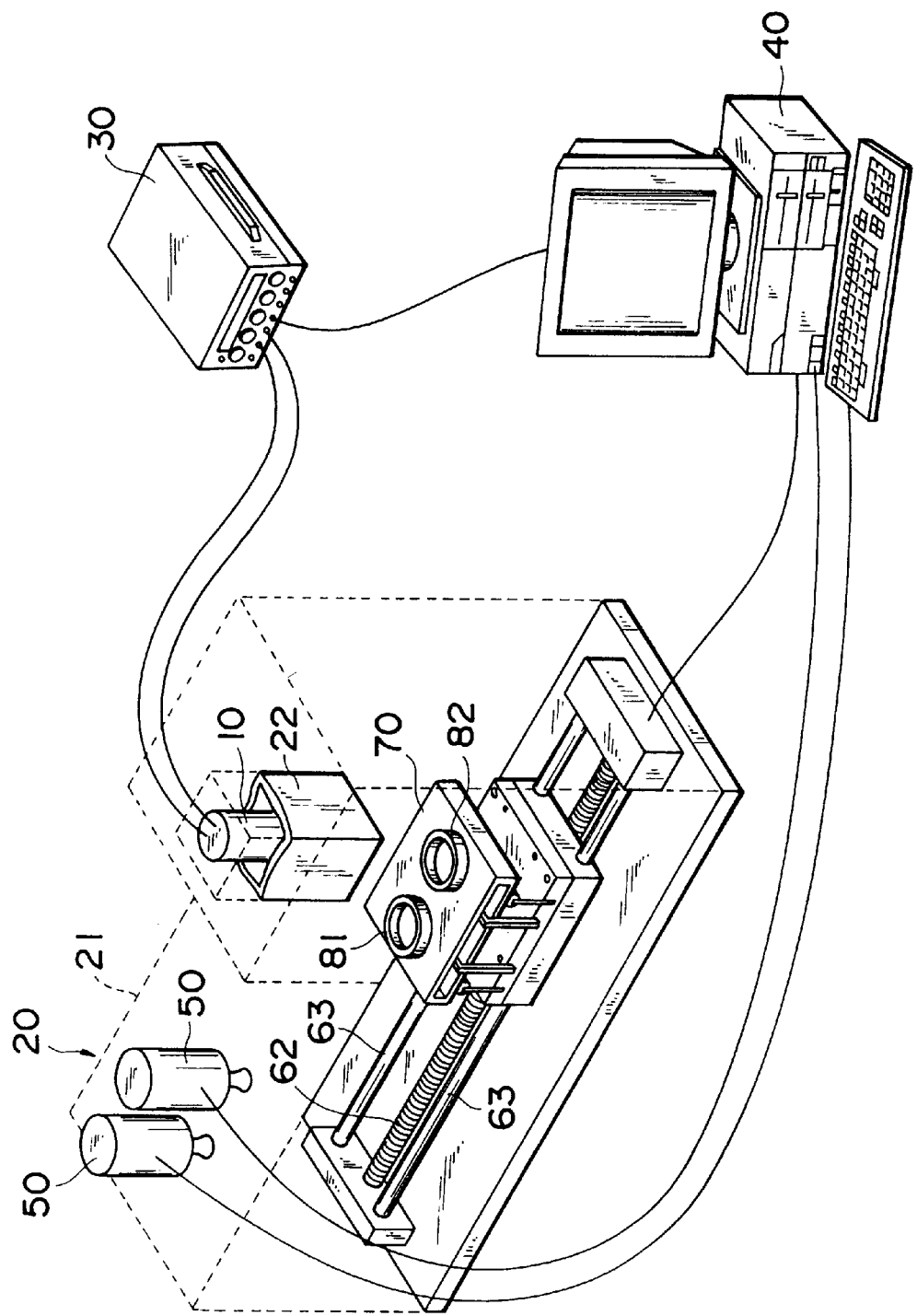
FIG. 4 is a schematic perspective view showing the structure of an apparatus according to a second embodiment of the present invention.

Then, the feed screw 62 of the seed conveying mechanism is rotated to move the sliding member 61 (located at an upper left side in FIG. 4) to a lower right side in FIG. 4 so as to locate the two samples of the seed in the Petri dishes 81 and 82 disposed on the stage 70 at predetermined positions. This movement is conducted in accordance with an instruction from the electronic computer 40.

Thereafter, for a predetermined period of time, the quantities of luminescence from the seeds are not measured, and the seeds are left standing still in dark. At this time, since no external light enters the interior of the ultra-weak luminescence detector 20 and the detector 20 is in a state of a dark chamber, the seeds may be left standing still in dark as they are. The period of time during which the seeds are left standing still may usually be 1 hour to 5 days. Most of seeds may suitably be left standing still for 1 to 3 days, while the still-standing time may intrinsically be determined depending on the variety of a plant to be used. Therefore, it is desirable to collect data on the still-standing time suitable for such a plant in advance by a preparatory experiment which is the same as that in the first embodiment. However, once the still-standing time suitable for the plant is determined, the resultant data can be used repeatedly in examinations to be conducted later.

Then, the shutter (not shown) of the housing 22 is opened in response to an instruction from the electronic computer 40 to detect ultra-weak luminescence from the respective seeds 80 by use of the PMT 10. At this time, the electronic computer 40 outputs an instruction to move the stage body 72 to a predetermined position so that either one of the microbe-inoculated seed and the reference seed is positioned right under the PMT 10. In this embodiment, the stage 70 may be moved every 5 seconds, so that the quantities of luminescence emitted from the seeds contained in the respective Petri dishes 81 and 82 may be measured. At this time, the total of the time for the measurement by the PMT 10 may be about 2 minutes. The PMT 10 may comprise a photomultiplier R208 (mfd. by Hamamatsu Photonics K.K.) and the measurement may be conducted under the same operational conditions as those used in the above-mentioned first embodiment.

Then, a pulse signal from the PMT 10 is binarized by the photon counter 30 and is transmitted to the electronic computer 40 to be recorded there as numerical data.

Then, the above-described procedure is repeated to obtain an predetermined amount of data suitable for the examination.

Next, in the electronic computer 40, recorded data are compared with each other to examine pathogen resistance of the plant. More specifically, this examination may be conducted in the following manner.

Thus, an average value of data obtained from the reference seed is represented by C (counts/sec), and a standard error of the data is represented by m (counts/sec). On the other hand, an average value of data obtained from the microbe-inoculated seed is represented by S (counts/sec), and a standard error of the data is represented by n (counts/sec). In this embodiment, the electronic computer 40 is programmed so as to judge that the bacterium to be examined imparts induced resistance to the plant used when (S−C)±(n+m) is always positive, and to judge that the microbe to be examined does not impart induced resistance to the plant when (S−C)±(n+m) is always negative. The thus obtained examination results are displayed on a monitor.

The above-mentioned examination method can also be conducted by using the apparatus for evaluating the ability of a microbe (such as non-pathogenic microbe) to impart pathogen resistance to a plant according to the first embodiment as described above. In a case where the above-mentioned apparatus is employed, the method to be used in combination therewith may also be conducted in the same procedure as that used in the first embodiment.

Next, a first example of the evaluation using a plant of Cucurbitaceae (melon family) will be described.

The seeds of Cucurbitaceae used in this Example were 4 kinds inclusive of melon, gourd, pumpkin, and cucumber.

The varieties of melon used in this Example were Earl's Favourite, Ooi, Burnett and Fukamidori. The variety of gourd used in this Example was Sennari. The varieties of pumpkin used in this Example were Shin-Tosa No.1 and Miyazu-Kurokawa. The variety of cucumber used in this Example was Shimoshirazu-Jibai. The bacterium to be evaluated was S-160 with respect to each of the above varieties of Cucurbitaceae. In addition, a bacterium Melon-27 was used for the variety of cucumber and the varieties of melon inclusive of Earl's Favourite, Ooi and Burnett. Further, *Fusarium oxysporum* A-1 ("I"-1) and S-52 were used for Earl's Favourite, a variety of melon. It has been already investigated that the *Fusarium oxysporum* S-52 exhibits remarkable induced resistance with respect to sweet potato and prevents the sweet potato from being infected with Fusarium wilt. It has also been investigated that the *Fusarium oxysporum* Melon-27 exhibits remarkable induced resistance with respect to melon.

Then, the evaluation method used in this Example will be described.

First, on Aug. 31, 1992, seeds of the respective varieties were sowed on a medium in Petri dishes 81 and 82.

Then, on Sep. 1, 1992, the above-mentioned respective bacteria to be evaluated were inoculated into germinated seeds of the above-mentioned respective varieties of plants as shown in the following Table 4. As a result, totally 20 kinds of samples (inclusive of non-inoculated samples) were prepared.

Then, on Sep. 2, 1992 (after about 16 hours counted from the inoculation of the bacteria), the germinated seeds of the above-mentioned respective varieties were evaluated by using the apparatus according to this embodiment. This evaluation was conducted in the manner as described above.

The evaluation results are shown in the following Table 4.

TABLE 4

| No. | Rooted seed | Variety | non-pathogenic microbe | Measured value (CPS) | Difference with non-inoculated sample | Reaction of variety |
|---|---|---|---|---|---|---|
| 1 | melon | Earl's Favorite | Non-inoculated | 324 ± 5.1 (N = 100) | — | |
| 2 | melon | Earl's Favorite | Melon-27 | 420 ± 3.1 (N = 100) | 96 ± 8.2 > 0 | induced resistance |
| 3 | melon | Earl's Favorite | "I"-1 | 447 ± 2.3 (N = 100) | 123 ± 7.4 > 0 | induced resistance |
| 4 | melon | Earl's Favorite | S-52 | 397 ± 2.1 (N = 100) | 73 ± 7.2 > 0 | induced resistance |
| 5 | melon | Earl's Favorite | S-160 | 331 ± 4.8 (N = 100) | 7 ± 9.9 | (induced resistance) |
| 6 | melon | Ooi | Non-inoculated | 207 ± 3.6 (N = 100) | — | |
| 7 | melon | Ooi | S-160 | 410 ± 6.0 (N = 100) | 203 ± 9.6 > 0 | induced resistance |
| 8 | melon | Ooi | Melon-27 | 361 ± 7.7 (N = 100) | 154 ± 11.3 > 0 | induced resistance |
| 9 | melon | Burnett | Non-inoculated | 172 ± 3.1 (N = 100) | — | |
| 10 | melon | Burnett | S-160 | 321 ± 2.3 (N = 100) | 149 ± 5.4 > 0 | induced resistance |

TABLE 4-continued

| No. | Rooted seed | Variety | non-pathogenic microbe | Measured value (CPS) | Difference with non-inoculated sample | Reaction of variety |
|---|---|---|---|---|---|---|
| 11 | melon | Burnett | Melon-27 | 316 ± 5.8 (N = 100) | 144 ± 8.9 > 0 | induced resistance |
| 12 | melon | Fukamidori | Non-inoculated | 125 ± 2.2 (N = 100) | — | |
| 13 | melon | Fukamidori | S-160 | 279 ± 2.7 (N = 100) | 154 ± 4.9 > 0 | induced resistance |
| 14 | gourd | Sennari | Non-inoculated | 176 ± 2.2 (N = 100) | — | |
| 15 | gourd | Sennari | S-160 | 216 ± 1.9 (N = 100) | 40 ± 4.1 | (induced resistance) |
| 16 | pumpkin | Shintosa No. 1 | Non-inoculated | 344 ± 2.3 (N = 100) | — | |
| 17 | pumpkin | Shintosa No. 1 | S-160 | 403 ± 8.9 (N = 100) | 59 ± 11.2 | (induced resistance) |
| 18 | cucumber | Shimoshirazu jibai | Non-inoculated | 224 ± 1.5 (N = 100) | — | |
| 19 | cucumber | Shimoshirazu jibai | S-160 | 616 ± 8.1 (N = 100) | 392 ± 9.6 > 0 | induced resistance |
| 20 | cucumber | Shimoshirazu jibai | Melon-27 | 563 ± 9.5 (N = 100) | 339 ± 11.0 > 0 | induced resistance |

As shown in the above Table 4, according to the judgement using this apparatus, when the *Fusarium oxysporum* Melon 27 was used for melon, the respective varieties of melon exhibited induced resistance. These results are consistent with those generally known in the art as described above. As a result, it has been found that the above-described method using this apparatus is very effective in evaluating the ability of a microbe (such as non-pathogenic microbe) to impart pathogen resistance to a plant.

In addition, the results as shown in the above Table 4 were also obtained with respect to reactions of the other varieties of slant with bacteria to be evaluated.

Next, a method for evaluating an agricultural chemical according to a third embodiment of the present invention will be described.

The apparatus to be used for this evaluation is the same as the apparatus according to the first or second embodiment as described above, except that a sprayer for containing and spraying an agricultural chemical is provided in this embodiment. The sprayer is juxtaposed with the other sprayers shown in FIG. 1 according to the first embodiment and is disposed on the upper surface of the casing. The method according to the third embodiment is conducted by using the apparatus which has the same basic structure as that of the first embodiment.

First, there are provided two kinds of samples, i.e., a sample of plant to be examined (hereinafter, referred to as "plant to be examined") into which an agricultural chemical has been absorbed, and a sample of the plant into which the agricultural chemical has not been absorbed. More specifically, samples of the plant to be examined are respectively accommodated in two Petri dishes which have been prepared beforehand. The Petri dishes containing these samples of the plant are placed on the upper surface of the stage provided in the ultra-weak luminescence detector. At this time, the samples of the plant are introduced into the interior of the ultra-weak luminescence detector through a door of the detector. After the Petri dishes are set on the upper surface of the stage, the door is perfectly closed so as to shield the interior of the detector from any external light.

Then, the agricultural chemical and distilled water among liquids contained in the sprayers are respectively sprayed on the samples of the plant to be examined. A first sprayer of the three sprayers disposed on the upper surface of the ultra-weak luminescence detector contains the agricultural chemical, a second sprayer contains distilled water, and a third sprayer contains an aqueous pathogen solution.

Accordingly, when the agricultural chemical is sprayed on one of the samples of the plant, the distilled water is sprayed on the other sample. Thus, there are provided a sample of the plant to be examined having absorbed the agricultural chemical (hereinafter, referred to as "agricultural chemical-absorbing plant"), and a sample of the plant not having absorbed the agricultural chemical (hereinafter, referred to as "reference plant").

Then, the samples of the plant to be examined are left standing for about 3 to 7 days. The reason for such standing is that it usually takes about 3 to 7 days for induced resistance to appear in a plant on the basis of the absorption of an agricultural chemical.

Then, the aqueous pathogen solution among the liquids contained in the sprayers is sprayed on the respective samples (i.e., the agricultural chemical-absorbing plant and the reference plant).

Next, the feed screw of the plant conveying mechanism is rotated to move the sliding member (located at an upper left side in FIG. 1) to a lower right side in FIG. 1, so that the two samples in the Petri dishes disposed on the upper surface of the stage are respectively located right under the corresponding PMTs. This movement is conducted in response to an instruction from the electronic computer.

Then, for a predetermined period of time, the quantities of luminescence from the samples are not observed and the samples are left standing still in dark. At this time, no external light enter the interior of the ultra-weak luminescence detector 20 and the interior of the detector is in a state of a dark chamber. Accordingly, the samples placed in the detector 20 may be left standing still in dark as they are. The period of time during which the samples are left standing still may usually be about 1 hour to 5 days, and most of samples may suitably be left standing still for about 1 to 3 days. Such a still-standing period of time may intrinsically be determined depending on the kind of plant. Accordingly, it is desired to collect data on the still-standing period in advance by using a preparatory experiment in the same manner as in the first embodiment. However, once such data is obtained, it can be used repeatedly in examinations to be conducted later.

Then, the shutters (not shown) of the housings 22 are opened in response to an instruction from the electronic computer 40 so as to detect ultra-weak luminescence emitted from the respective samples by the corresponding PMTs. At this time, the period of time for the measurement by the PMTs is 1 minute. The PMTs and their operational conditions therefor are the same as those used in the first embodiment.

Then, pulse signals from the respective PMTs are binarized by the corresponding photon counters and are transmitted to the electronic computer to be recorded there as numerical data.

Next, in the electronic computer, the recorded data are compared with each other to examine pathogen resistance of the plant induced by the agricultural chemical. More specifically, this examination is conducted in the following manner. Thus, an average value of data obtained from the reference sample is represented by C (counts/sec), and a standard error of such data is represented by m (counts/sec). On the other hand, an average value of data obtained from the agricultural chemical-absorbing sample is represented by S (counts/sec), and a standard error of such data is represented by n (counts/sec). The electronic computer is programmed so as to judge that the agricultural chemical has activated pathogen resistance of the plant to a higher degree, as a value of S±n is remoter from C±m; and to judge that the agricultural chemical is not suitable for the activation of pathogen resistance of the plant, as a value of S±n is nearer to C±m. The thus obtained examination results are displayed on a monitor.

Then, a first example of the evaluation using yam (root tuber or tuberous root) will be described.

The first example is an application of the present invention to a screening method for an agricultural chemical.

The agricultural chemicals used in this Example were Olizemate (probenazol) and Polyoxin-AL. The pathogen to be used for inoculation was a blue rot pathogen, *Penicillium sclerotigenum* Yamamoto.

Then, this evaluation method will be described.

First, on Aug. 25, 1992, yam was treated with each of the agricultural chemicals.

On Sep. 1, 1992, the blue rot pathogen was inoculated into predetermined samples of yam, and totally 6 samples (inclusive of samples not inoculated with the pathogen) were prepared.

On Sep. 2, 1992 (after about 16 hours counted from the inoculation of the pathogen), the evaluation was conducted by using the apparatus according to this embodiment. The evaluation method was the same as described hereinabove.

The evaluation results are shown in the following Table 5.

TABLE 5

| No. | Inoculated pathogen | Agricultural chemical | Measured value (CPS) |
|---|---|---|---|
| 1 | blue rot pathogen | non-treated | 496 ± 2.5 (N = 100) |
| 2 | blue rot pathogen | Olizemate 200 ppm | 653 ± 8.3 (N = 100) |
| 3 | blue rot pathogen | polyoxin 200 ppm | 507 ± 8.0 (N = 100) |

As shown in the above Table 5, the following results were obtained by measuring the quantities of luminescence from the plant by use of the apparatus according to this embodiment. The sample which had absorbed 200 ppm of the Olizemate showed an increase of 157 (counts/sec) in the auantity of luminescence, and the sample which had absorbed 200 ppm of the polyoxin showed an increase of 11 (counts/sec) in the quantity of luminescence, as compared with that for the sample which had not absorbed the agricultural chemical.

Accordingly, it has been found that the apparatus according to this embodiment is applicable to a method for screening an agricultural chemical capable of directly or indirectly activating induced resistance of a plant.

A second example of the evaluation using sweet potato will be described.

The variety of sweet potato used in this Example was Beniazuma. The pathogen used in this Example was pathogen of Fusarium wilt. The non-pathogenic microbes used in this Example were S-160 and S-52 as described hereinabove. It has been investigated that the S-52 exhibits induced resistance to Stem rot (*Fusarium oxysporum* f. sp. *batatas*) of sweet potato.

In addition, olizemate and polyoxin were used as agricultural chemicals for examining induced resistance of sweet potato to Stem rot.

The method for this examination will be described.

On Sep. 1, 1992, the above-described bacteria were respectively inoculated to slices (or cut pieces) of the sweet potato. As a result, totally 8 samples (inclusive of samples not inoculated with the pathogen) were prepared.

On Sep. 2, 1992 (after about 16 hours counted from the inoculation of the bacteria), the slices of the sweet potato were examined by using the apparatus according to this embodiment. The method for this examination was conducted by repeating Steps 201 to Step 207 (FIG. 2) as described above.

The examination results are shown in the following Table 6.

TABLE 6

| No. | Inoculated microbe | Agricultural chemical | Measured value (CPS) |
|---|---|---|---|
| 1 | Non-inoculated | non-treated | 390 |
| 2 | Stem rot | non-treated | 2400 |
| 3 | S-52 | non-treated | 2700 |
| 4 | S-160 | non-treated | 2513 |
| 5 | Non-inoculated | Olizemate 1000 ppm | 390 |
| 6 | Non-inoculated | Polyoxin 200 ppm | 510 |
| 7 | Stem rot | Olizemate 200 ppm | 1500 |
| 8 | Stem rot | Polyoxin 200 ppm | 2760 |

As shown in Sample Nos. 1 to 4 in the above Table 6, it has been confirmed by the apparatus according to this embodiment that the *Fusarium oxysporum* S-52 exhibits induced resistance to Stem rot of sweet potato. It has also been confirmed by the apparatus according to this embodiment that the bacterium S-160 exhibits induced resistance to Stem rot of sweet potato in the same manner as in S-52.

As shown in Sample Nos. 5 to 8 in the above Table 6, it has been confirmed by the apparatus according to this embodiment that when the sample 80 was not inoculated with the bacterium, the quantity of luminescence from the sample 80 treated with 1000 ppm of Olizemate was not different from that of the sample 80 not treated with the agricultural chemical. On the other hand, it has been confirmed that when the sample 80 was treated with 200 ppm of polyoxin, the quantity of luminescence from the sample 80 was increased by about 120 cps (counts/sec). It has been confirmed by the apparatus according to this embodiment that when the sample 80 was inoculated with Stem rot pathogen, the quantity of luminescence emitted from the sample 80 treated with 1000 ppm of Olizemate (it has been confirmed that the Olizemate imparts induced resistance to rice plant) was decreased by 900 cps as compared with the sample 80 not treated with the agricultural chemical, while the quantity of luminescence emitted from the sample 80 treated with 200 ppm of polyoxin was increased by 360 cps.

Thus, the apparatus according to this embodiment is effectively applicable to the screening of an agricultural chemical capable of imparting induced resistance, in the same manner as in the first evaluation example.

Then, various experiments were conducted in order to more specifically analyze a state of luminescence in this Example. These experiments were conducted in the following manner.

Figure 5:
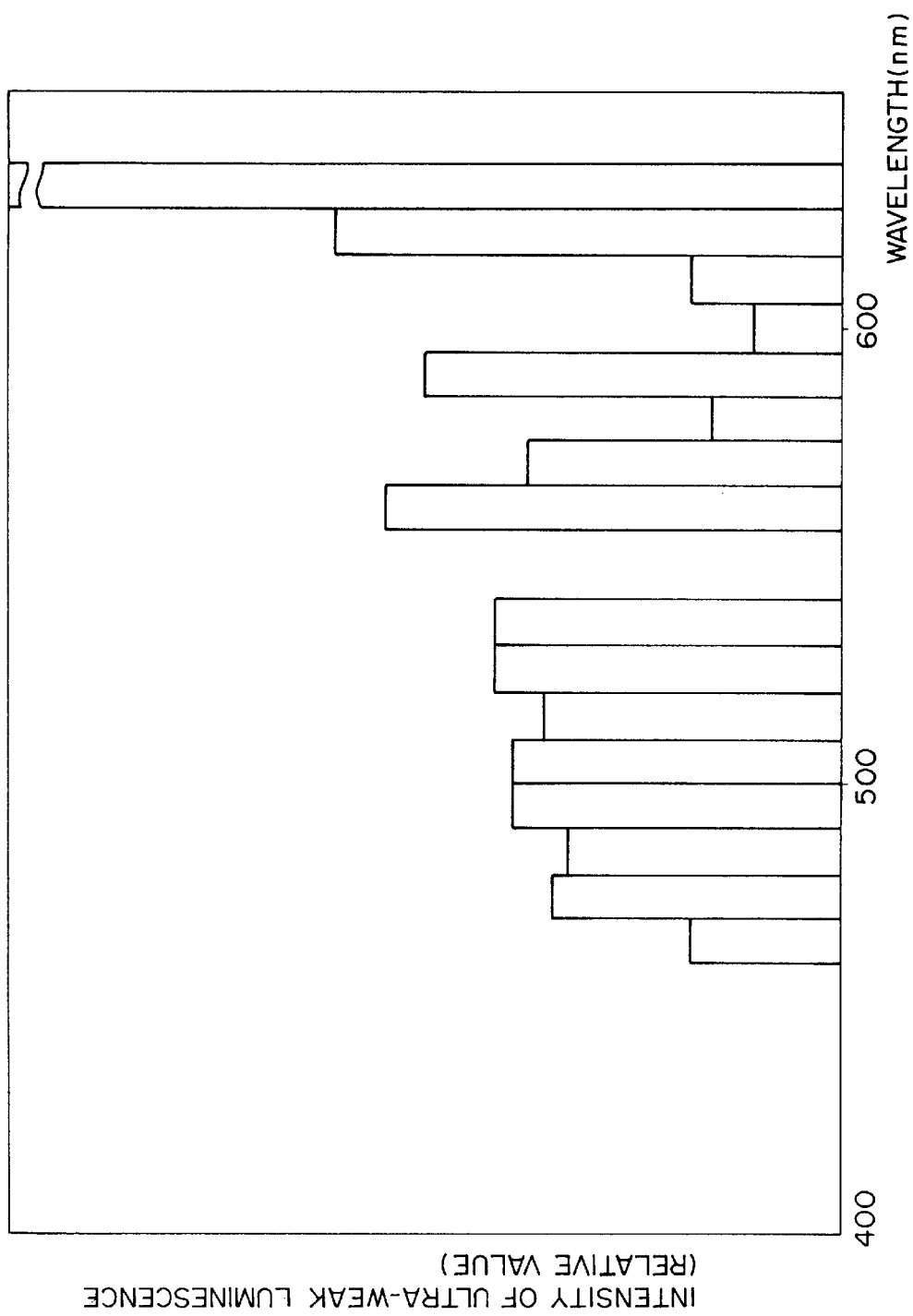
FIG. 5 is a graph showing a distribution of a luminescence spectrum.

First, chemical species relating to the luminescence was investigated. In this Example, the chemical species relating to the luminescence was investigated by using a method for measuring ultra-weak light spectrum (i.e., a cut-off filter method described in "Recent progress in ultra-weak light measurement and spectral information analyzing technique, and its application to medicine and biological science", by Fumio Inaba, $O_{plus}E$, No. 12, page 78 (1980) published by Shin-Gijutsu Communications K.K.). Various cut-off filters were used in this measurement. In general, since a change in the quantity of luminescence directly depends on transmissivity or permeability of the respective cut-off filters and quantum efficiency of a photomultiplier, a correction was made to the measurement results. When the quantity of luminescence was corrected in a predetermined manner, a luminescence spectrum shown in FIG. 5 was obtained. As shown in FIG. 5, the spectrum is extended over a range of from 460 nm to 600 nm. These results are very similar to a distribution of a luminescence spectrum obtained from a germinated plant seed which one of the present inventors has measured ("Special Issue: Light and Biological Science; Ultra-weak luminescence from germinated roots", by Mitsuo Hiramatsu, $O_{plus}E$, No. 149, pp 105–110 (1992)).

Figure 6:
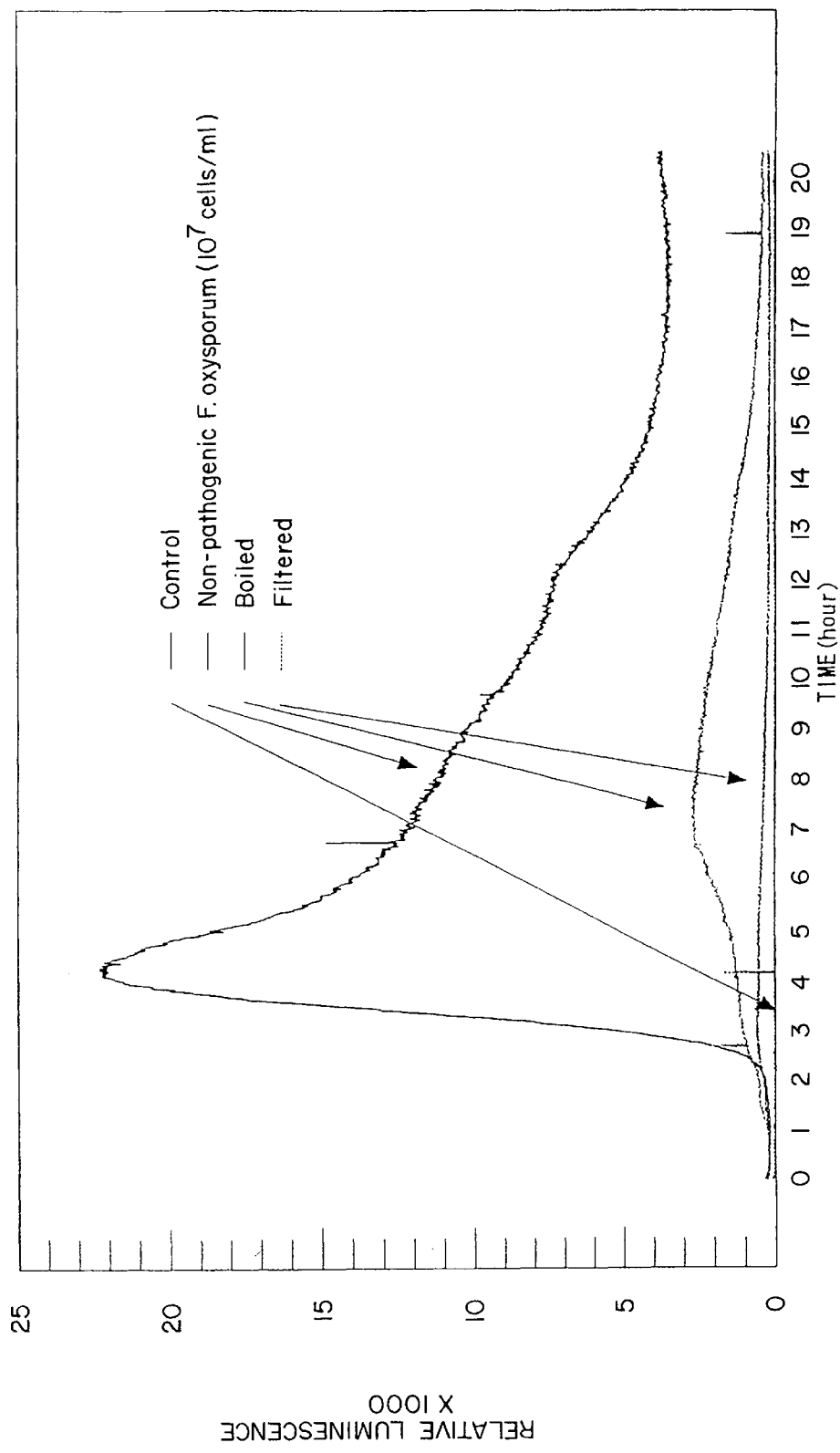
FIG. 6 is a graph showing dynamics and relative intensity of luminescence emitted from each of sweet potato slices inoculated with living cells of non-pathogenic *F. oxysporum* ($10^7$ cells/ml), boiled cells of non-pathogenic *F. oxysporum* ($10^7$ cells/ml), and a filtered liquid culture of non-pathogenic *F. oxysporum* ($10^7$ cells/ml), respectively, and a sweet potato slice (control) which has not been inoculated with *F. oxysporum*.

FIG. 6 shows a change in the interaction between non-pathogenic *F. oxysporum* and sweet potato slices with the elapse of time. As shown in FIG. 6, the sweet potato slice inoculated with living cells of the non-pathogenic *F. oxysporum* ($10^7$ cells/ml) showed a much larger luminescence peak after about four (4) hours counted from the inoculation of the *F. oxysporum*, as compared with those observed in the cases of a control (a sweet potato slice not inoculated with *F. oxysporum*), a "boiled" sample (a sweet potato slice inoculated with boiled cells of *F. oxysporum* ($10^7$ cells/ml)), and a "filtered" sample (a sweet potato slice inoculated with a filtered liauid culture of *F. oxysporum* ($10^7$ cells/ml).

Figure 7:
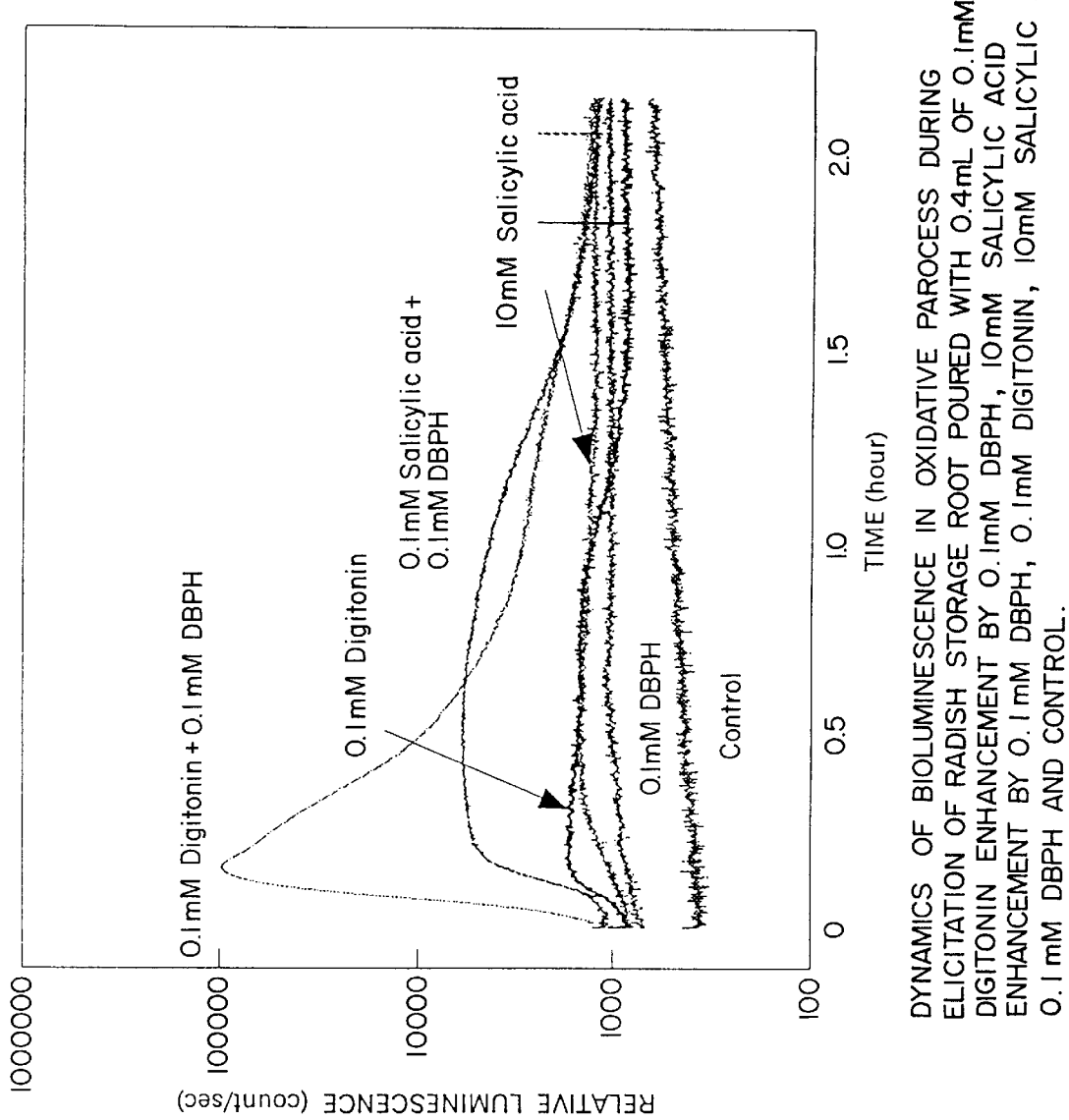
FIG. 7 is a graph showing dynamics of luminescence in an oxidative process during elicitation of radish storage root poured with 0.4 ml of 0.1 mM digitonin enhancement by 0.1 mM DBPH (4-(5,6-Dimethoxy-2-benzothiazolyl) phthalylhydrazide), 10 mM salicylic acid enhancement by 0.1 mM DBPH, 0.1 mM digitoxin, 10 mM salicylic acid, 0.1 mM DBPH, and control.

FIG. 7 shows a fact that the peak appearing after 5–15 min. counted from the inoculation of a microbe could be enhanced by a chemiluminescence reagent (i.e., a reagent for detecting $H_2O_2$ and/or superoxide anion) of DBPH, and the luminescence emitted from a radish storage root which had been treated with one selected from various elicitors generally used in the art could be enhanced by DBPH in a similar manner.

Figure 8:
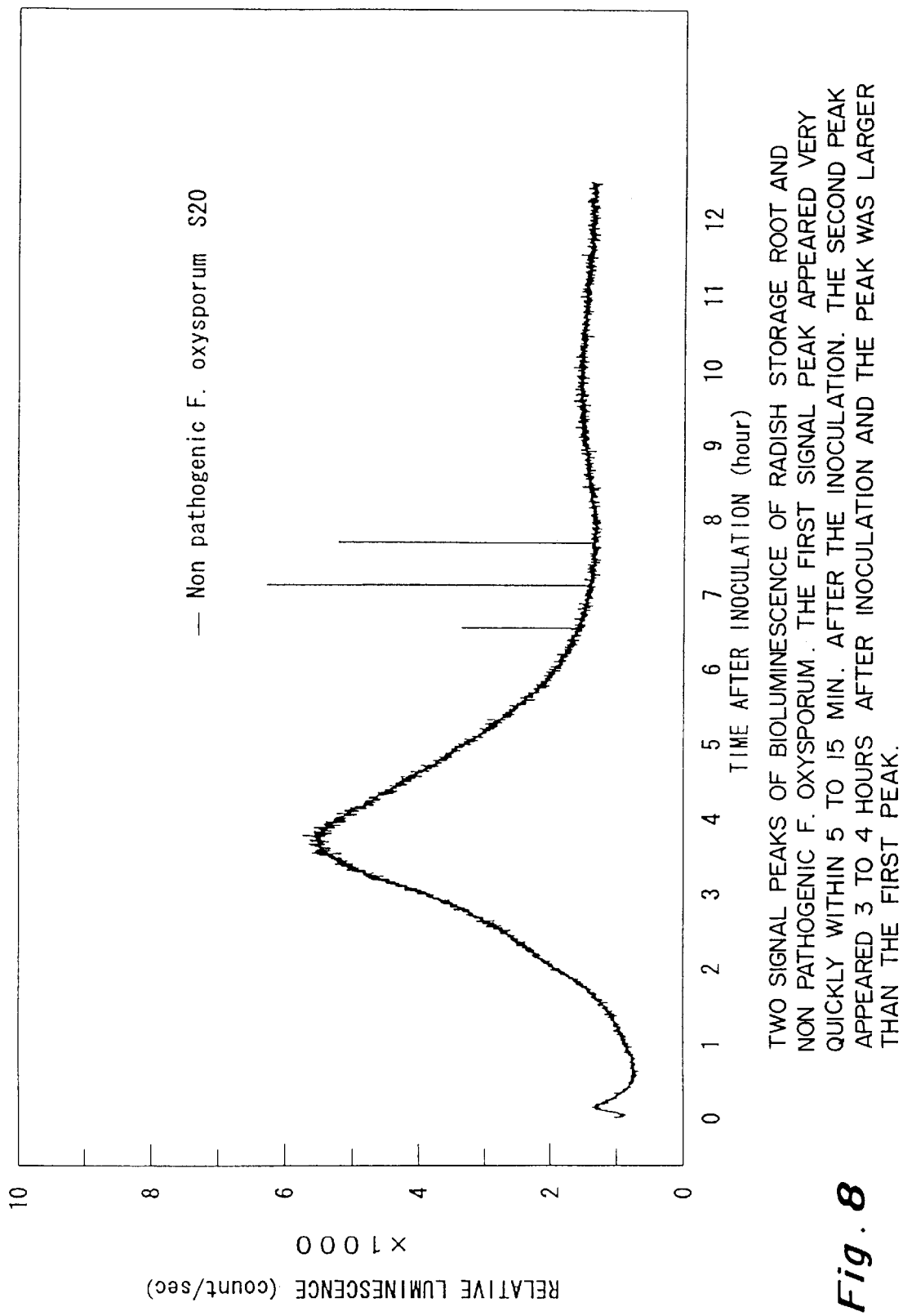
FIG. 8 is a graph showing two signal peaks of luminescence emitted from radish storage root inoculated with non-pathogenic *F. oxysporum*, wherein the first signal peak appears very quickly within 5 to 15 min. after the inoculation of *F. oxysporum*, and the second peak appears 3 to 4 hours after the inoculation of *F. oxysporum*. The second peak is larger than the first peak.

FIG. 8 shows a change in the interaction between non-pathogenic *F. oxysporum* and a radish storage root with the elapse of time. As shown in FIG. 8, a first smaller peak appeared after about 5–15 min. counted from the inoculation of the *F. oxysporum*, and a second larger peak appeared after about 3–4 hours counted from the inoculation of the *F. oxysporum*. According to the present inventors' investigation, the larger second peak in FIG. 8 was not enhanced by the addition of DBPH. In consideration of the results shown in FIG. 8 in combination with the results as shown in FIG. 7, it is considered that the first peak in FIG. 8 corresponds to the luminescence based on active oxygen chemical species, while the second peak in FIG. 8 corresponds to the luminescence based on another chemical species.

Since the luminescent system comprises a plant, i.e., a biological body, and has a very complicated mechanism, it is difficult to completely identify the chemical species relating to the luminescence (luminescent chemical species). However, it can be seen from the above spectrum that one of the luminescent chemical species may contain active oxygen species.

In the above-described examination Examples, an individual plant body was used as the sample 80. However, a biological species other than an individual plant, such as protoplast, callus and cultured cell may also be used as the sample 80.

In some cases, it is not easy to discriminate resistance and/or susceptibility because of small quantity of luminescence emitted from the sample 80 to be examined. For example, when resistance, etc, to virus is examined, a difference between the quantities of luminescence emitted from predetermined samples is small as compared with that for mold and bacterium. In such a case, it is desired to follow a change in the reaction between a plant and a virus with the elapse of time so that the quantity of luminescence may be measured at a point of time after the inoculation where a maximum quantity of luminescence is provided. In a case where the discrimination is not easy even when such a conditior is selected, it is preferred to use a so-called luminescence sensitizer such as luminol. Since the luminol reacts with active oxygen and changes a luminescence spectrum so as to draw photons, which are self-absorbed by a plant per se and cannot be detected, the luminol resultantly has a function of increasing the quantity of luminescence.

As described above, when the apparatus or method according to this embodiment is used, ultra-weak luminescence emitted from the sample 80 positioned on the sample mount 61 is detected by the PMT 10, and an output signal from the PMT 10 is converted into a digital signal by the photon counter 30, and the resultant digital signal is processed by the electronic computer 40 to be converted into numerical data. In other words, according to the apparatus or method according to this embodiment, the ultra-weak luminescence from the sample 80 is converted into numerical data, and based on the value, resistance of the plant is judged on the basis of the resultant numerical data. As a result, the resistance of a plant may be quantitatively examined with ease by utilizing ultra-weak luminescence.

In this embodiment, in all the Examples, ultra-weak luminescence is detected by a photon counting method using the photon counter 30, but another photodetecting method of low noise and high susceptibility for detecting ultra-weak luminescence may also be used. In all the examples of this embodiment, zero-dimensional (or zero-order) measurement using the PMT 10 is employed, but multi-dimensional measurement using a one-dimensional sensor and/or a two-dimensional sensor may be employed alternatively. For example, it is particularly preferred that a plurality of samples are prepared by using a titration plate (or titer plate) having a plurality of (preferably, a large number of) concavities (or wells), and a large number of the samples 80 are simultaneously subjected to screening by using a two-dimensional ultra-high susceptibility television camera.

As specifically described hereinabove, when a method according to the present invention is used, at least one sample of a plant to be examined is divided into at least two divisions, one division (first division) thereof is caused to contact a reagent such as pathogen, non-pathogenic microbe and agricultural chemical, another division (second division) which is not caused to contact such a reagent, and the first and second divisions are left standing under a predetermined condition for a predetermined period of time. Accordingly, there is provided a difference in the quantity of ultra-weak luminescence emitted from the samples between the first and second divisions, depending on the degree of an interaction between the plant and the reagent such as pathogen. In the present invention, the quantities of ultra-weak luminescence from the two divisions of samples are measured, and the thus measured quantities of ultra-weak luminescence are compared with each other. As a result, according to the present invention, pathogen resistance or pathogen susceptibility of the plant to be examined may be evaluated for a short period of time easily and objectively.

According to the present invention, there is also provided an apparatus comprising:

inoculating means for inoculating a microbe (such as pathogen and non-pathogenic microbe) on a first division divided from at least one sample of a plant to be examined;

sample leaving means for leaving a second division divided from the at least one sample not inoculated with the microbe and the first division inoculated with the microbe, for a predetermined period of time under a predetermined condition;

first and second photodetecting means for respectively measuring the quantities of luminescence emitted from the first and second divisions which have been left standing by the sample leaving means; and examining means for comparing the quantities of the luminescence respectively measured by the first and second photodetecting means, thereby to examine the resistance or susceptibility of the plant to the microbe.

Accordingly, when the above-mentioned apparatus according to the present invention is used, the first division of the sample inoculated with the microbe and the second division not inoculated with the microbe are treated under the same environment, and the respective ultra-weak luminescence emitted from the first and second divisions may be measured for a short period of time simultaneously and easily. As a result, the examination may be conducted objectively and accurately.

According to the present invention, there is further provided an apparatus comprising:

first and second sample positioning means for positioning a first division and a second division divided from at least one sample of a plant to be examined;

inoculating means for inoculating a microbe (such as pathogen and non-pathogenic microbe) on the first division;

sample leaving means for leaving the second division not inoculated with the microbe and the first division inoculated with the microbe, for a predetermined period of time under a predetermined condition;

a photodetector disposed so as to be opposed alternately to either of the first and the second sample positioning means for detecting luminescence emitted from either of the first and second divisions which have been left standing by the sample leaving means;

measuring means for alternately receiving an output of the photodetector in synchronism with switching of the first and second sample positioning means to be disposed opposite to the photodetector, thereby to measure the quantities of luminescence respectively emitted from the first and second divisions; and examining means for comparing the quantities of the luminescence measured by the measuring means, thereby to examine the resistance or susceptibility of the plant to the microbe.

Accordingly, when the above apparatus according to the present invention is used, ultra-weak luminescence emitted from the first and second divisions of the sample may be measured substantially simultaneously for a short period of time, even by using a single photodetector. As a result, according to the present invention, the resistance of a plant may be examined by utilizing ultra-weak luminescence emitted from the plant, and therefore the resistance of a plant may be examined sufficiently quantitatively even by using a plant at a stage of germinated seed. In other words, according to the present invention, it is not necessarily required to grow the plant to its seedling. Therefore, when the resistance of a plant is intended to be examined, it is not necessary to take a long period of time, which has been required in the prior art.

In the present invention, since the examination can be conducted at a stage of germinated seed of a plant and it is not necessary to grow the plant to be examined to a seedling, much labor and a vast site required for the growth of a large number of samples of the plant are not necessary.

In addition, since the resistance can be examined at a stage of geminated seed of an object to be examined, it is easy to grow and examine the object under the same environmental conditions.

Thus, according to the present invention, it is possible that a pathogen such as mold and bacterium is inoculated into a plant and the resultant ultra-weak luminescence emitted from the plant is detected, and the thus obtained detection results are converted into numerical data, thereby to quantitatively examine the biological property (such as resistance and susceptibility to a microbe) of the plant. In addition, according to the present invention, the resistance of a plant to be induced by the inoculation of a non-pathogenic microbe or weak-pathogenic microbe may be quantitatively subjected to screening, and/or the resistance of a plant to be activated by distribution of an agricultural chemical may be quantitatively subjected to screening.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application No. 279042/1992 filed on Oct. 16, 1992 is hereby incorporated by reference.

What is claimed is:

1. A method for examining pathogen resistance or pathogen susceptibility of a plant, comprising the steps of:

dividing at least one sample of germinating seed of a plant to be examined into at least two divisions and shielding the at least two divisions from any external light, inoculating a pathogen comprising mold on a first division of the at least two divisions of the sample, leaving the first division standing in the dark for a predetermined period of time and measuring the quantity of luminescence ($S_1$) emitted from the first division;

inoculating a second division of the at least two divisions with substantially no pathogen and leaving said second division of the at least two divisions of the sample standing in the dark for a predetermined period of time, and measuring the quantity of luminescence ($C_1$) emitted from the second division; and comparing the quantities of the luminescence emitted from the first and second divisions of the sample, thereby to examine the resistance or susceptibility of the plant to the pathogen in a manner such that when $S_1 > C_1$, the plant to be examined is judged to have pathogen resistance, and when $C_1 > S_1$, the plant to be examined is judged to have pathogen susceptibility.

2. A method according to claim 1, wherein $n_1$ is the standard error of $S_1$ and $m_1$ is the standard error of $C_1$ and when $(S_1 - C_1) \pm (n_1 + m_1)$ is always positive, the plant to be examined is judged to have pathogen resistance, and when $(S_1 - C_1) \pm (n_1 + m_1)$ is always negative, the plant to be examined is judged to have pathogen susceptibility.

3. The method of claim 1, wherein the predetermined period of time is between 1 hour and 5 days.

4. An apparatus for examining pathogen resistance or pathogen susceptibility of a plant, comprising:

first sample positioning means for positioning a first division divided from at least one sample of germinating seed of a plant to be examined;

second sample positioning means for positioning a second division divided from the sample of germinating seed of the plant;

inoculating means for inoculating a pathogen comprising mold on the first division;

sample leaving means for leaving the second division positioned by the second sample positioning means and the first division inoculated with the pathogen and positioned by the first sample positioning means, for a predetermined period of time under a predetermined condition;

first photodetecting means disposed opposite to the first sample positioning means for measuring the quantity of luminescence ($S_1$) emitted from the first division which has been left standing by the sample leaving means;

second photodetecting means disposed opposite to the second sample positioning means for measuring the quantity of luminescence ($C_1$) emitted from the second division which has been left standing by the sample leaving means; and examining means for comparing the quantities of the luminescence measured by the first and second photodetecting means, thereby to examine the resistance or susceptibility of the plant to the pathogen in a manner such that when $(S_1) > (C_1)$, the plant to be examined is nudged to have pathogen resistance, and when $(C_1) > (S_1)$, the plant to be examined is judged to have pathogen susceptibility.

5. An apparatus according to claim 4, wherein $n_1$ is the standard error of $S_1$ and $m_1$ is the standard error of $C_1$ and when $(S_1 - C_1) \pm (n_1 + m_1)$ is always positive, the plant to be examined is judged to have pathogen resistance, and when $(S_1 - C_1) \pm (n_1 + m_1)$ is always negative, the plant to be examined is judged to have pathogen susceptibility.

6. An apparatus for examining pathogen resistance or pathogen susceptibility of a plant, comprising:

first sample positioning means for positioning a first division divided from at least one sample of germinating seed of a plant to be examined;

second sample positioning means for positioning a second division divided from the sample of germinating seed of the plant;

inoculating means for inoculating a pathogen comprising mold on the first division;

sample leaving means for leaving the second division positioned by the second sample positioning means and the first division inoculated with the pathogen and positioned by the first sample positioning means, for a predetermined period of time under a predetermined condition;

a photodetector disposed so as to be opposed alternately to either of the first ($S_1$ or $C_1$) emitted from either the first or second divisions which has been left standing by the sample leaving means;

measuring means for alternately receiving an output from the photodetector in synchronism with switching of the first and second sample positioning means to be disposed opposite to the photodetector, thereby to respectively measure the quantities of luminescence ($S_1$ and $C_1$) emitted from the first and second divisions; and examining means for comparing the quantities of the luminescence respectively emitted from the first and second divisions, which have been measured by the measuring means, thereby to examine the resistance or susceptibility of the plant to the pathogen in a manner such that when $(S_1) > (C_1)$, the plant to be examined is judged to have pathogen resistance, and when $(C_1) > (S_1)$ the plant to be examined is judged to have pathogen susceptibility.

7. An apparatus according to claim 6, wherein $n_1$ is the standard error of $S_1$ and $m_1$ is the standard error of $C_1$ and when $(S_1 - C_1) \pm (n_1 + m_1)$ is always positive, the plant to be examined is judged to have pathogen resistance, and when $(S_1 - C_1) \pm (n_1 + m_1)$ is always negative, the plant to be examined is judged to have pathogen susceptibility.

* * * * *